United States Patent [19]

Brinkerhoff et al.

[11] Patent Number: 4,612,933

[45] Date of Patent: Sep. 23, 1986

[54] MULTIPLE-LOAD CARTRIDGE ASSEMBLY FOR A LINEAR SURGICAL STAPLING INSTRUMENT

[75] Inventors: Ronald J. Brinkerhoff, Moscow; Rudolph H. Nobis, Cincinnati, both of Ohio

[73] Assignee: Senmed, Inc., Cincinnati, Ohio

[21] Appl. No.: 595,291

[22] Filed: Mar. 30, 1984

[51] Int. Cl.$^4$ ............................................. A61B 17/04
[52] U.S. Cl. ................................. 128/334 R; 227/19; 227/DIG. 1
[58] Field of Search ....................... 128/334 R, 334 C; 227/DIG. 1, 19, 135

[56] References Cited

U.S. PATENT DOCUMENTS

| | | | |
|---|---|---|---|
| 3,601,302 | 8/1971 | Potekhina et al. | 227/DIG. 1 X |
| 4,086,926 | 5/1978 | Green et al. | 128/334 R |
| 4,202,480 | 5/1980 | Annett | 227/DIG. 1 X |
| 4,296,881 | 10/1981 | Lee | 227/DIG. 1 X |
| 4,391,401 | 7/1983 | Moshofsky | 227/DIG. 1 X |
| 4,412,539 | 11/1983 | Jarvik | 227/DIG. 1 X |

FOREIGN PATENT DOCUMENTS 2075411 11/1981 United Kingdom ............ 128/334 R

Primary Examiner—Michael H. Thaler
Attorney, Agent, or Firm—Frost & Jacobs

[57] ABSTRACT

A multiple-load cartridge assembly for use with a linear surgical stapling instrument of the type which, when actuated, simultaneously implants at least one row of staples in the tissue of a patient and forms or clinches the staples of the row against the instrument anvil. The cartridge assembly comprises a cartridge having a row of staple-containing forming pockets and a driver having a plurality of blades equal in number to the number of forming pockets and configured to drive the staples from the forming pockets through the tissue to be sutured and against the instrument anvil to be clinched, when the surgical stapling instrument is actuated. The cartridge has at least one row of storage pockets, equal in number to the forming pockets, and each containing at least one staple. An indexing mechanism is provided to shift the at least one staple in each storage pocket to the line of action between the driver and the anvil after the first actuation of the surgical stapling instrument, for at least another actuation of the surgical stapling instrument. A safety interlock within the cartridge assembly assures correct sequential operation of the cartridge assembly and prevents jamming thereof. An indicator visually shows the number of the load of staples ready to be implanted and formed.

50 Claims, 70 Drawing Figures

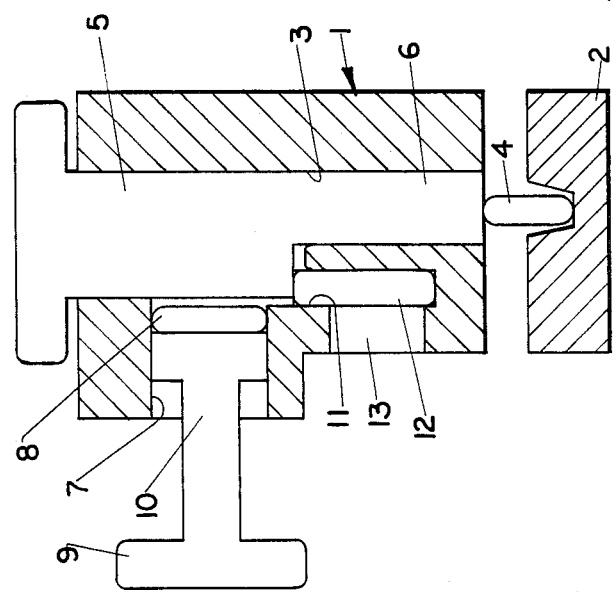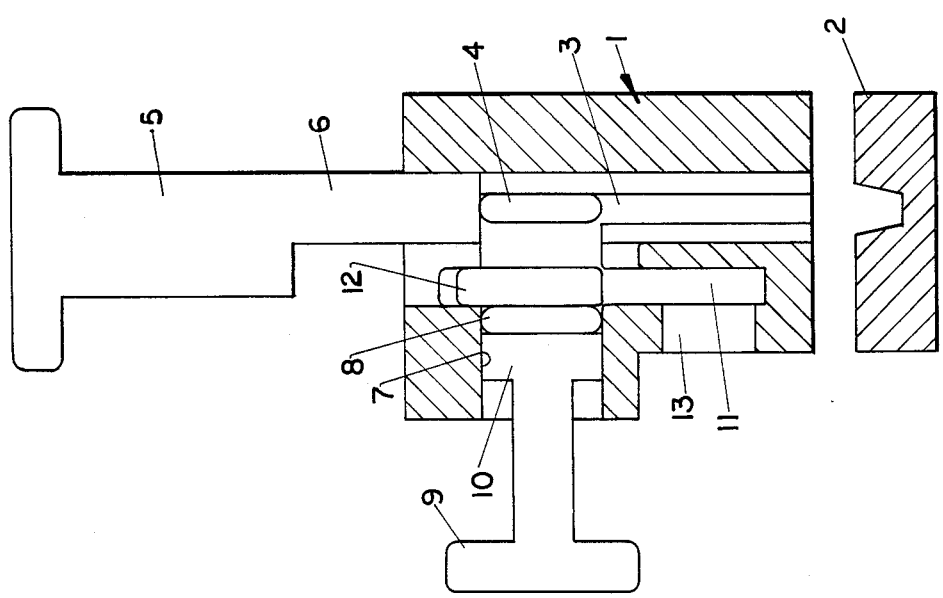

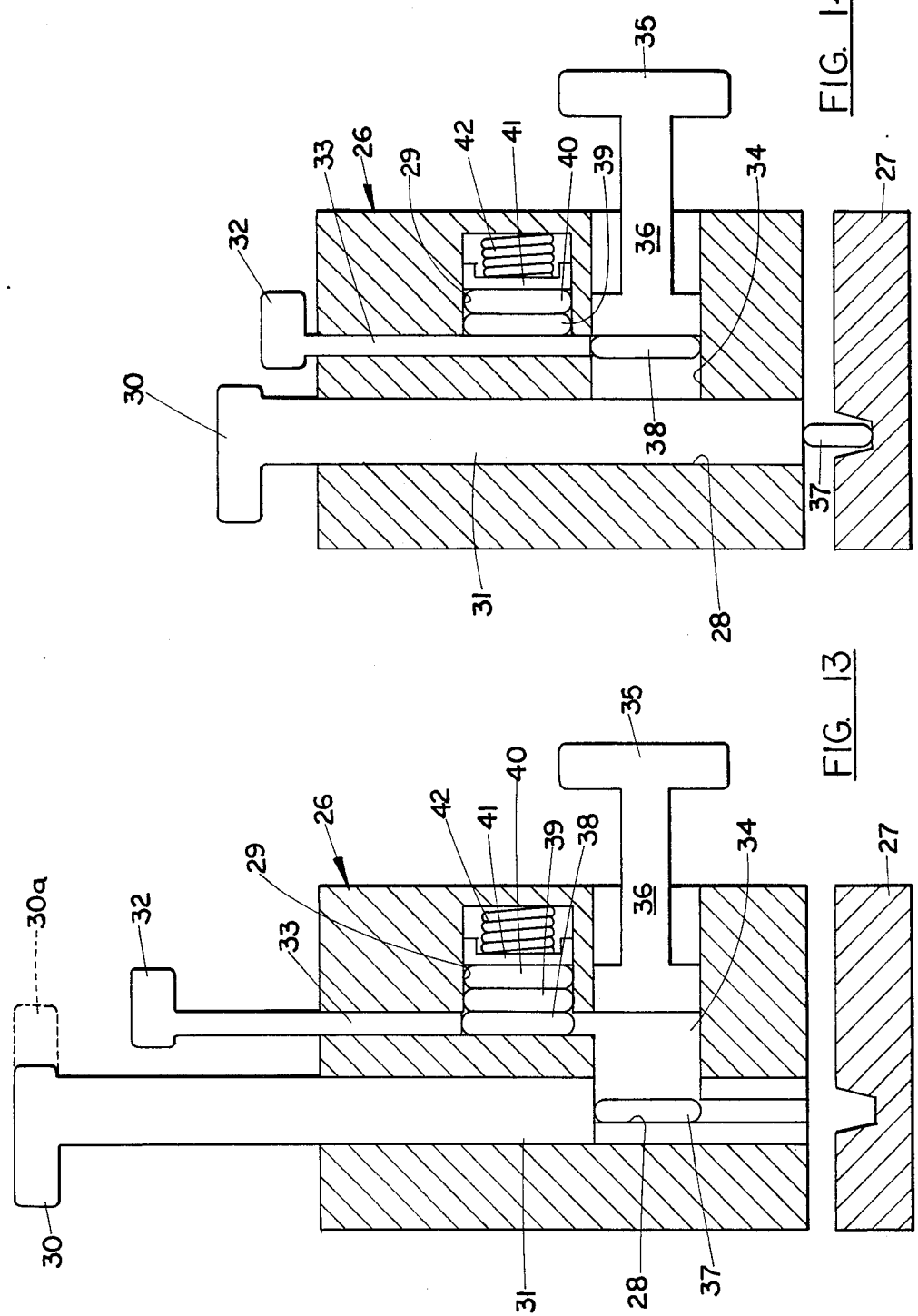

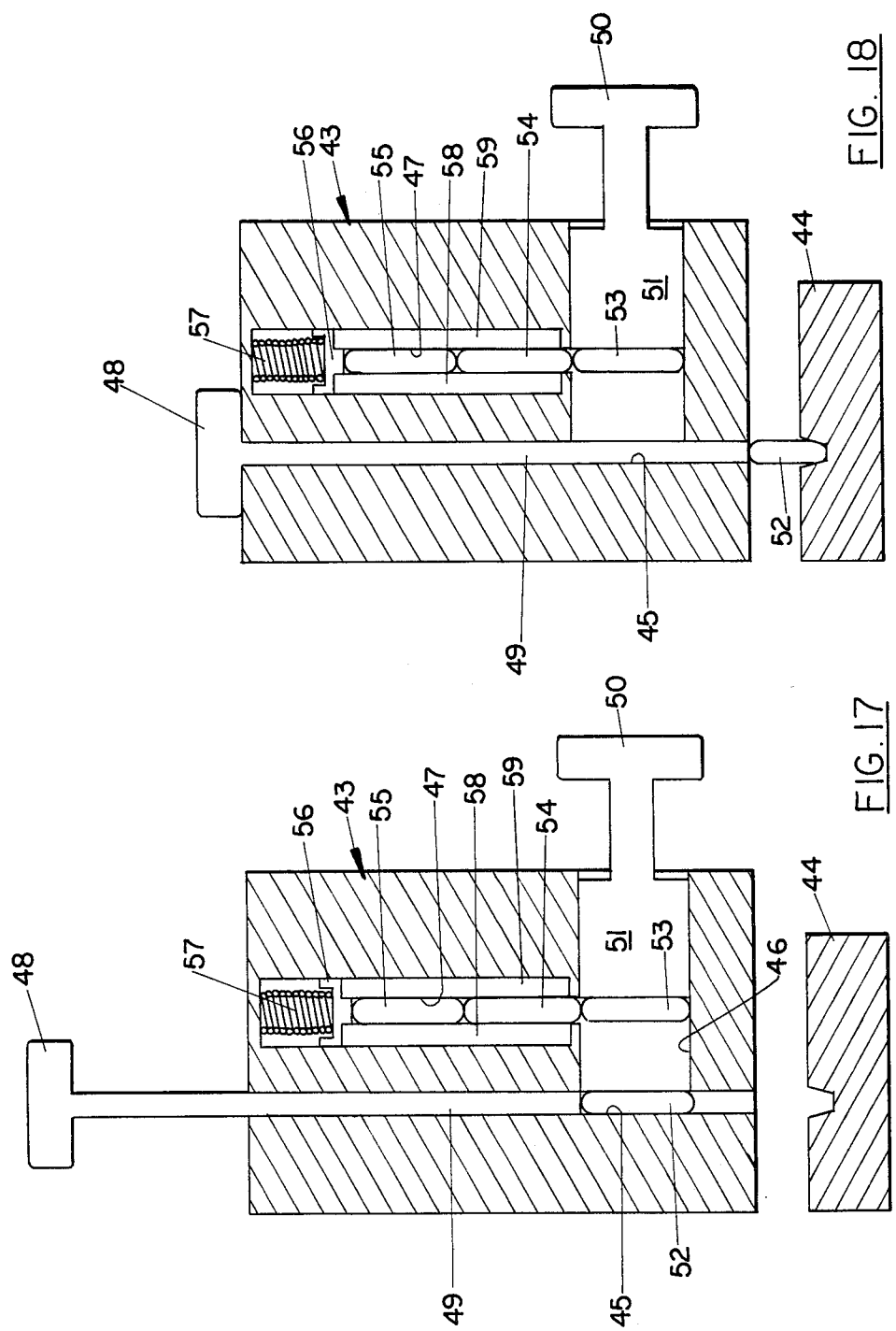

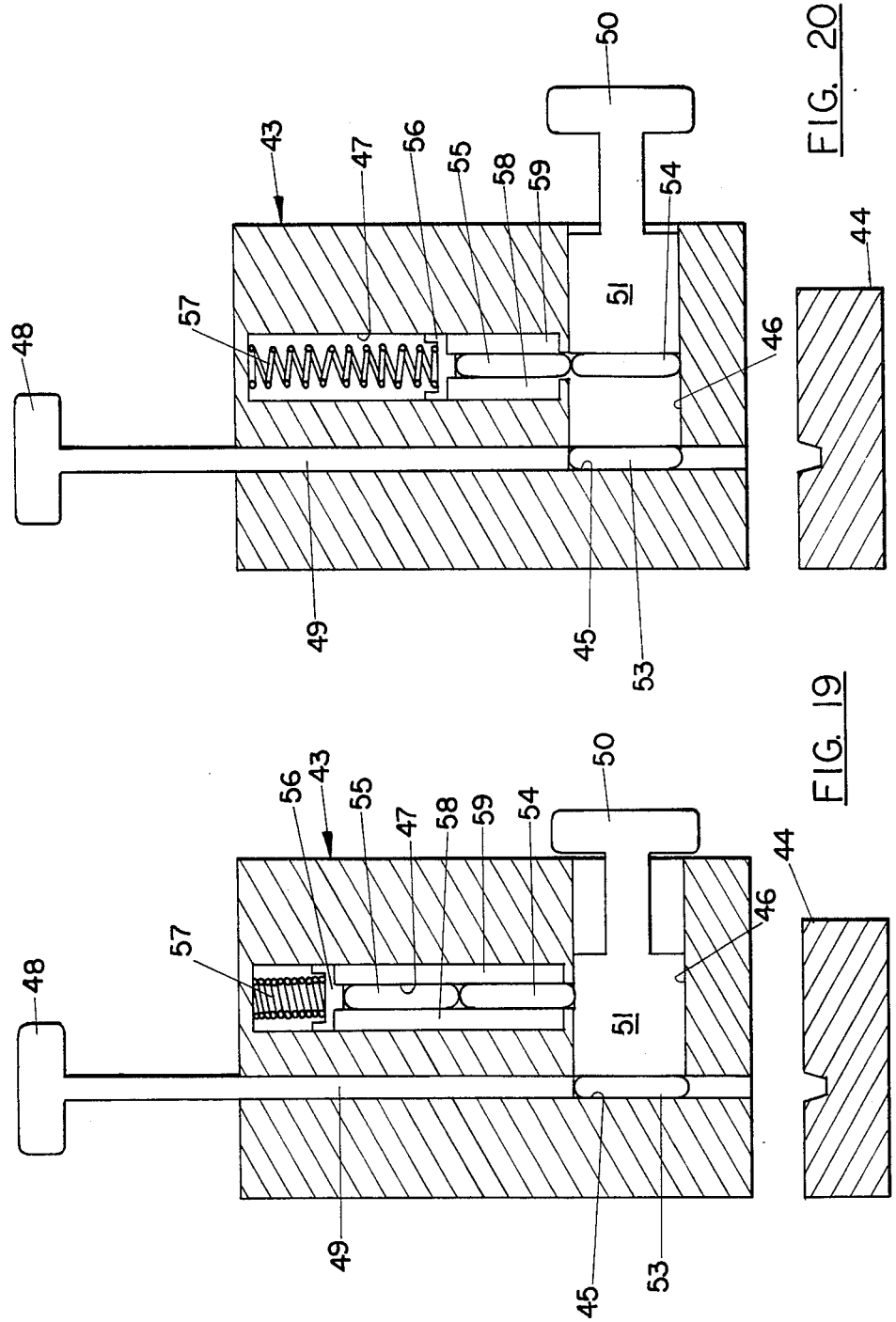

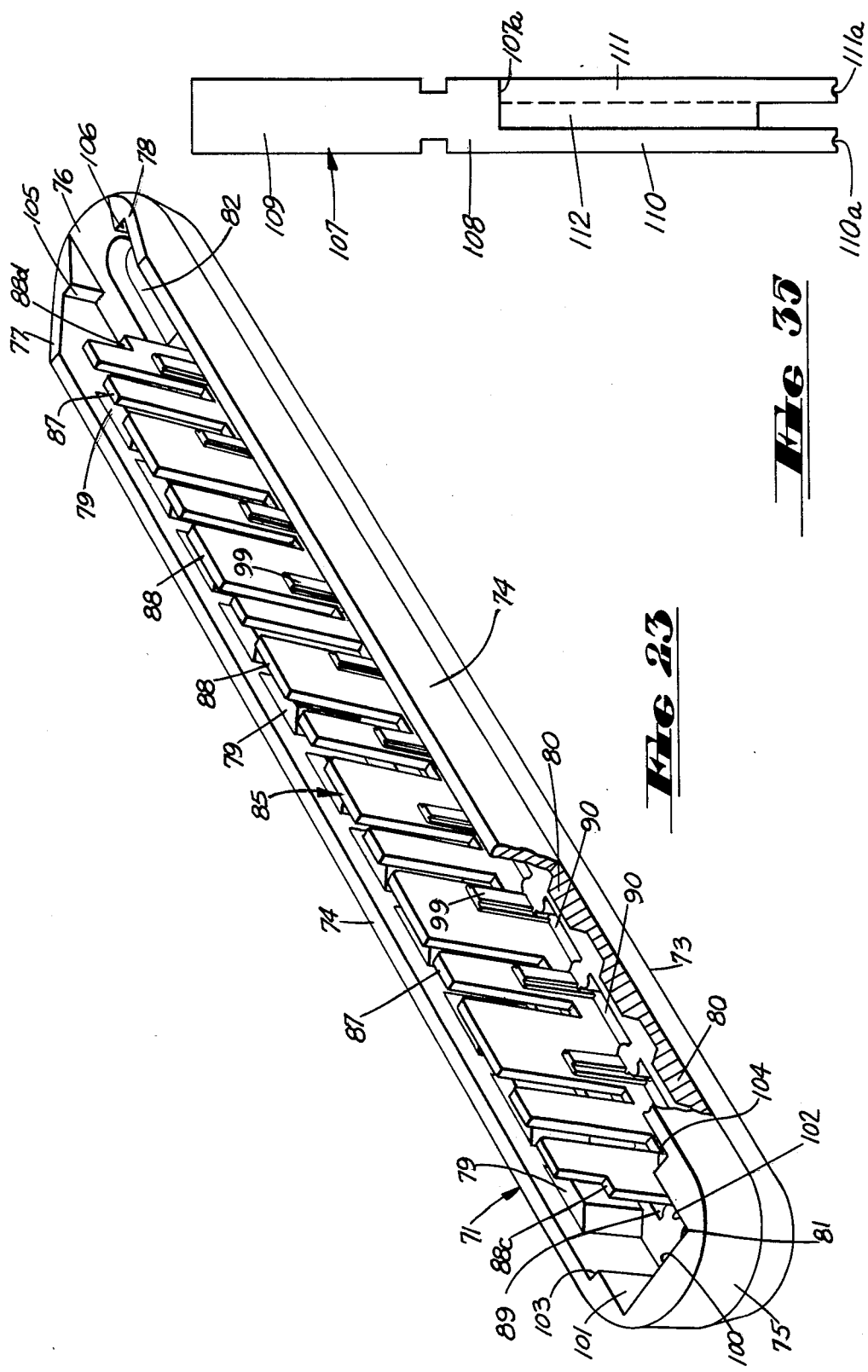

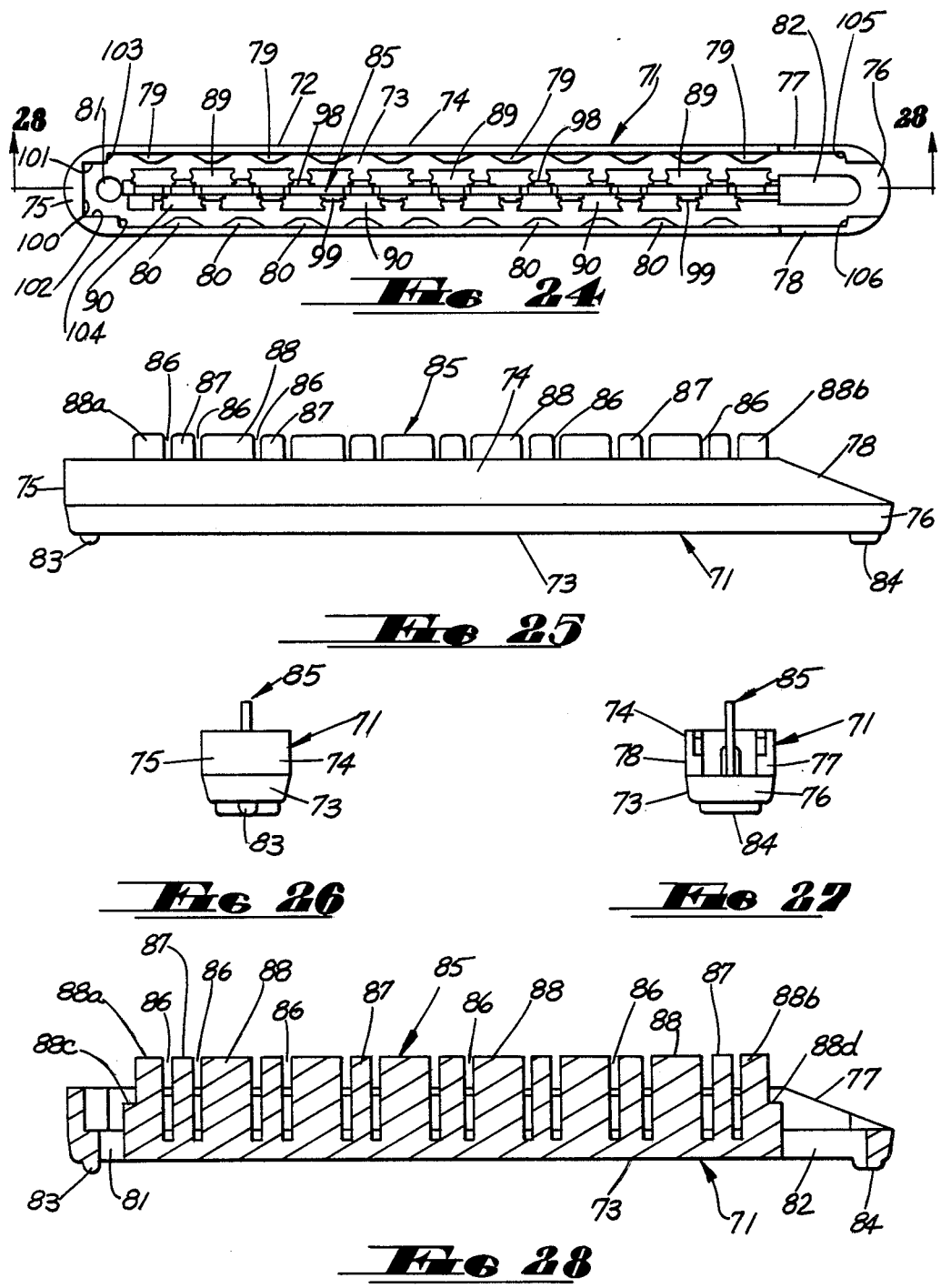

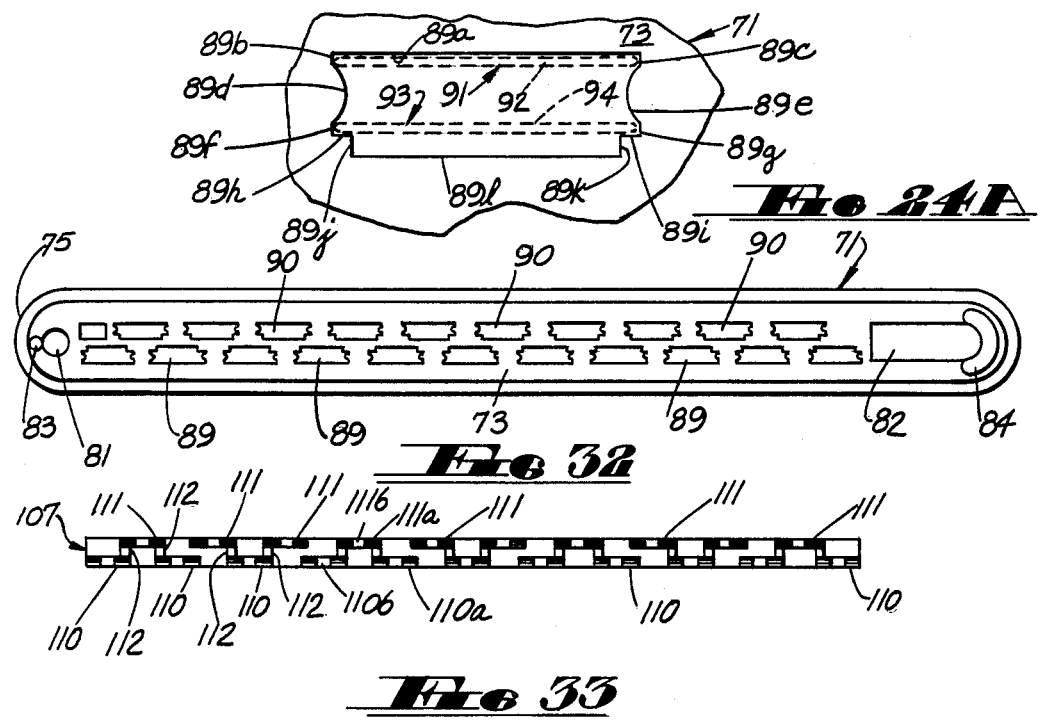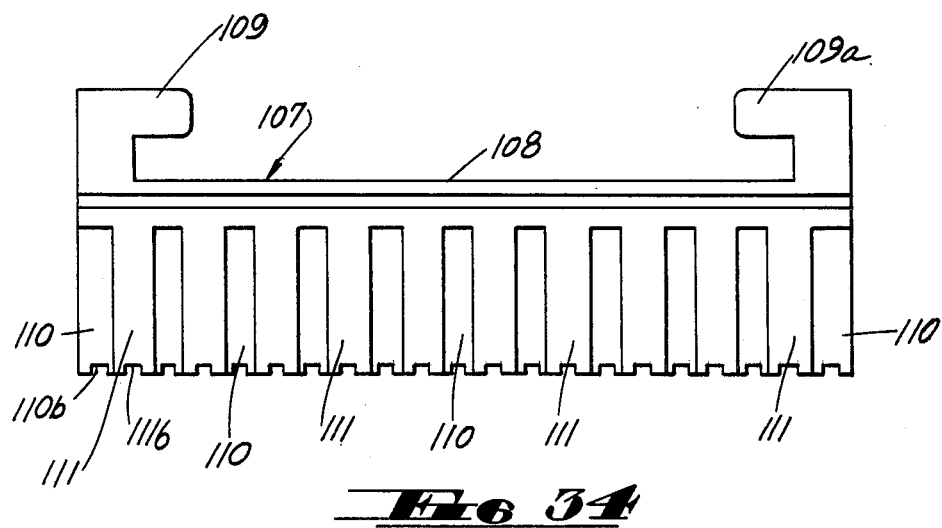

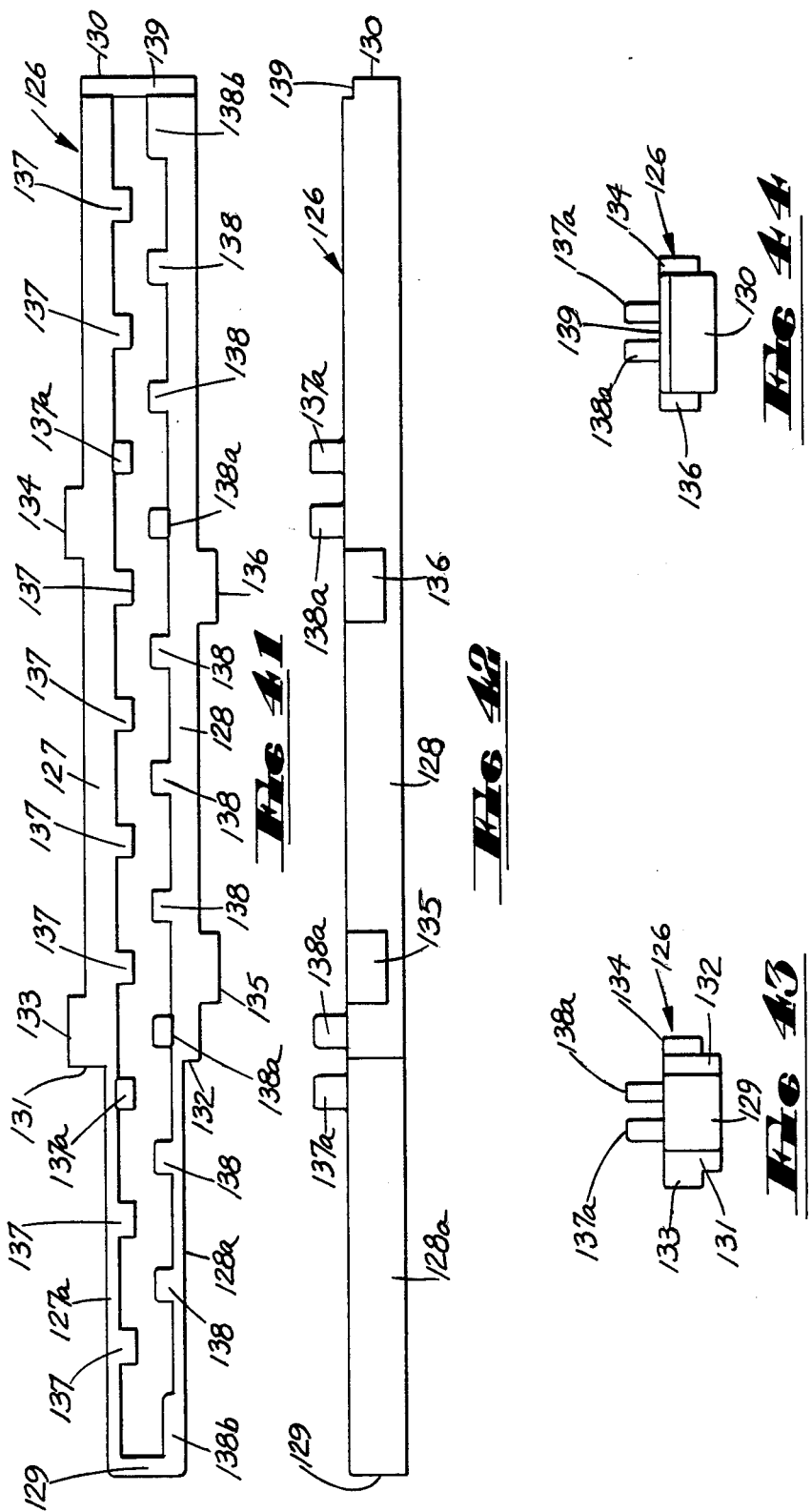

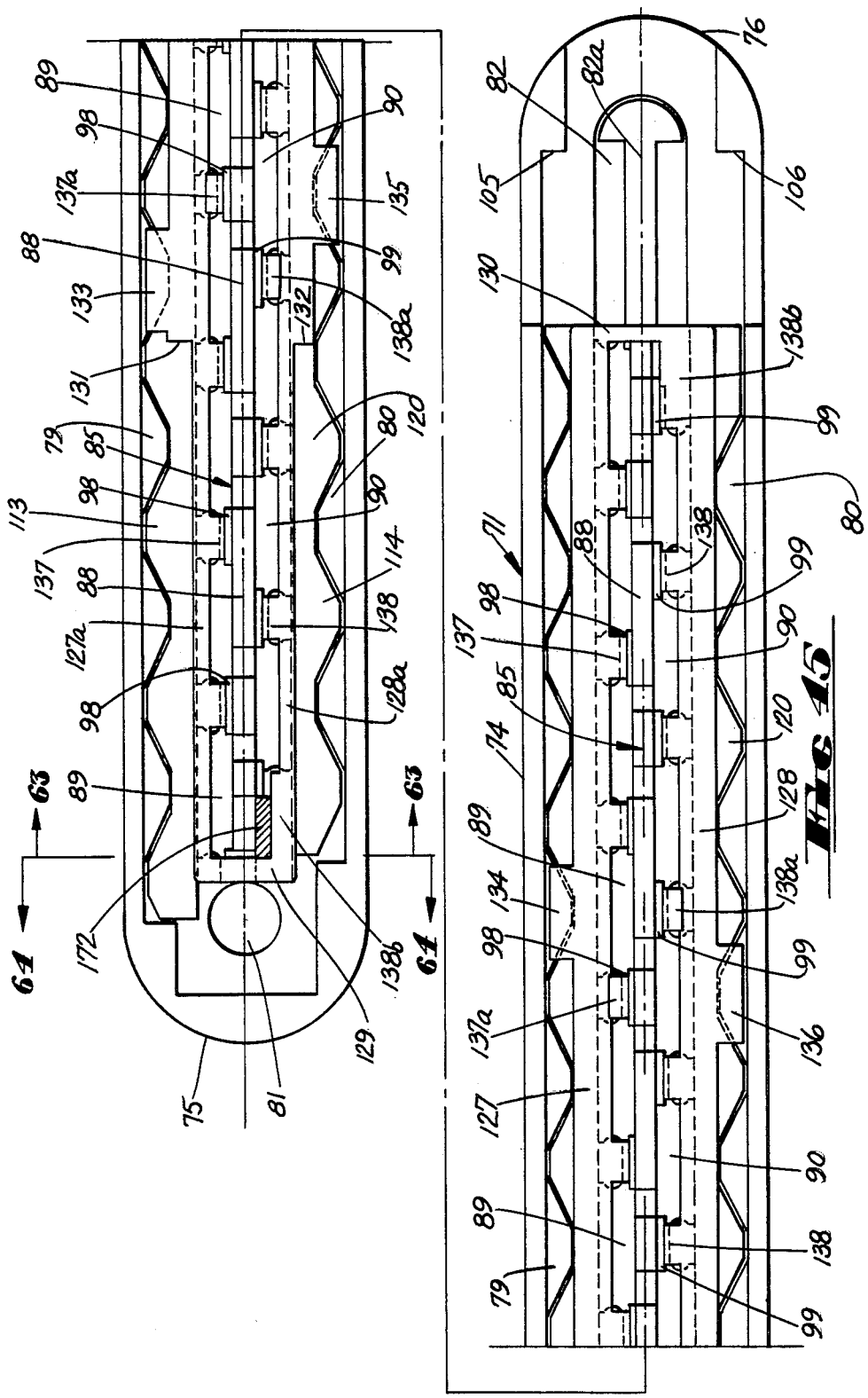

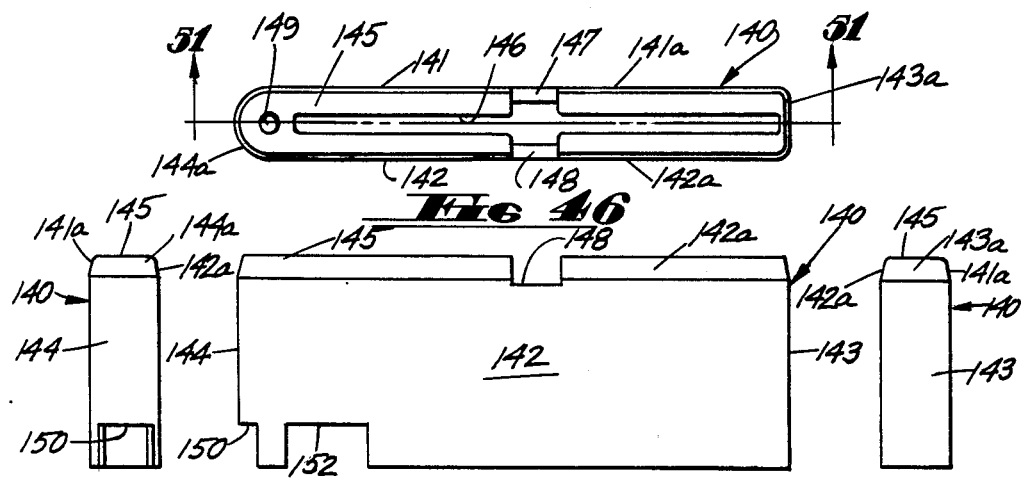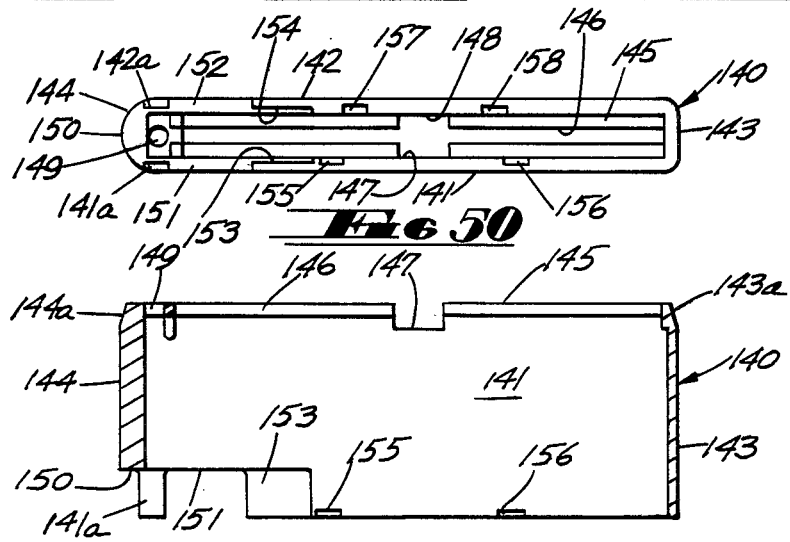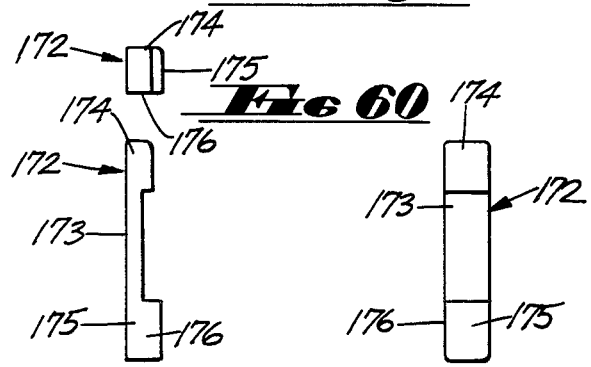

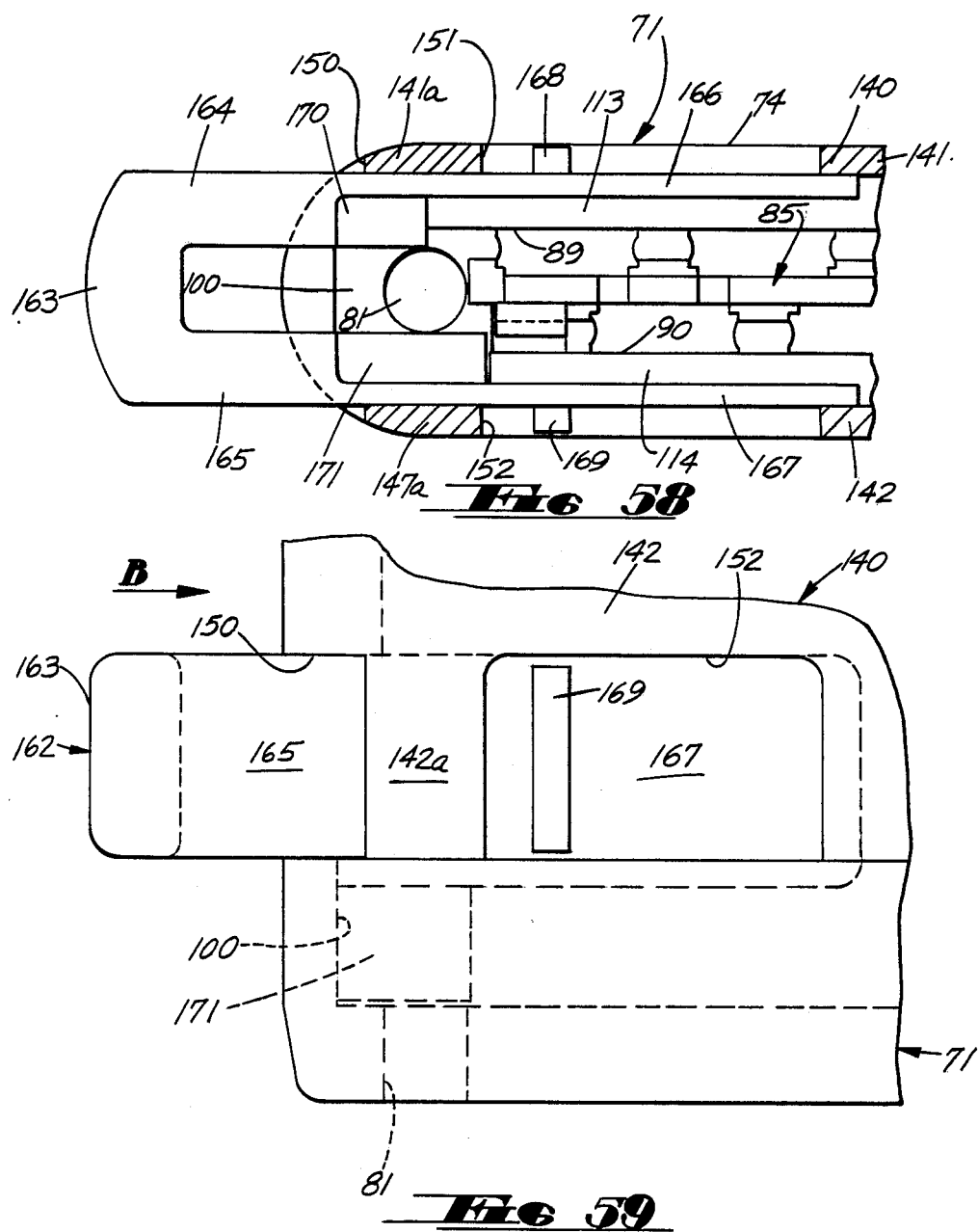

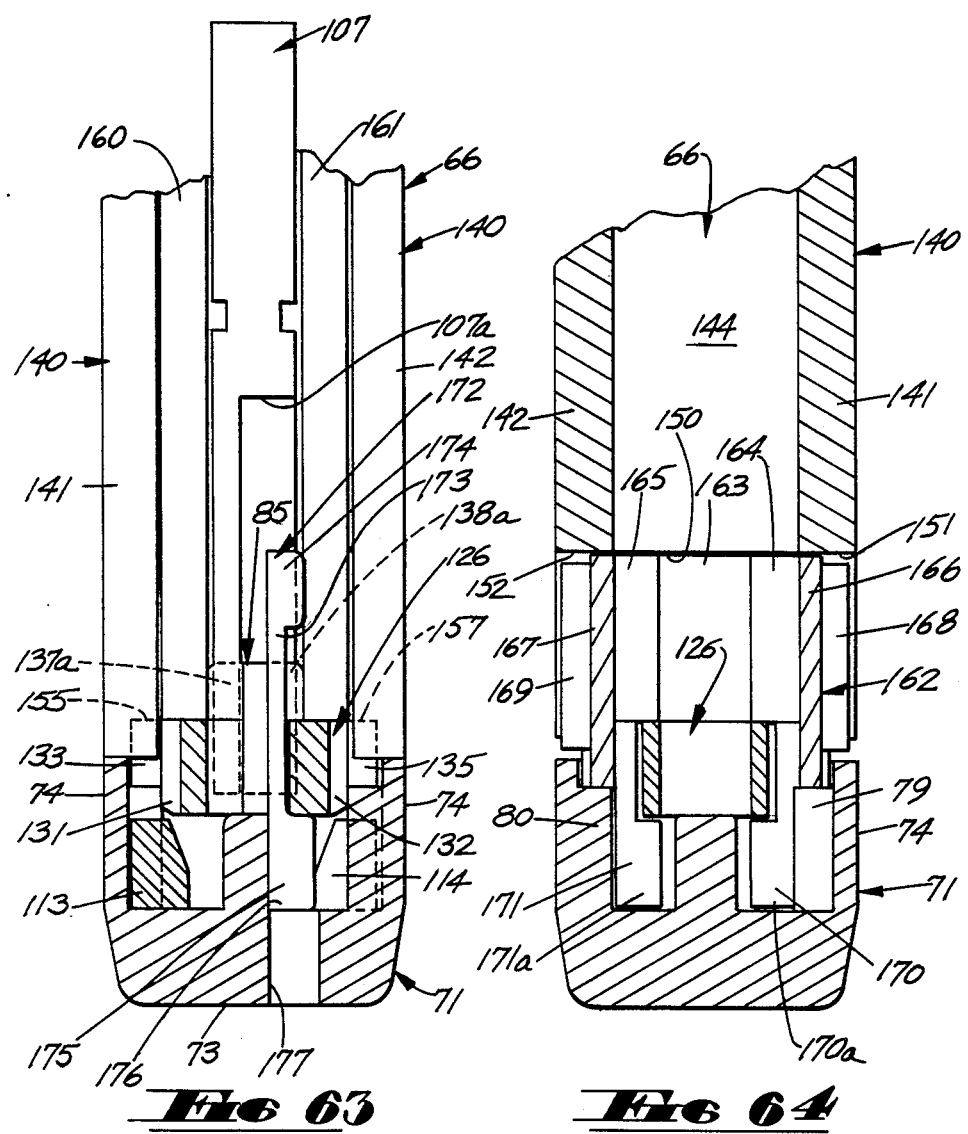

MULTIPLE-LOAD CARTRIDGE ASSEMBLY FOR A LINEAR SURGICAL STAPLING INSTRUMENT

TECHNICAL FIELD

The invention relates to a cartridge assembly for a linear surgical stapling instrument, and more particularly to such a cartridge assembly containing more than one load of surgical staples, thereby enabling the surgical stapling instrument to be actuated more than once before changing surgical stapling instruments or reloading or replacing the cartridge.

BACKGROUND ART

In recent years, there has been an increasing number of surgeons using surgical staples, rather than conventional sutures. This is true because the use of surgical staples and surgical stapling instruments has rendered many difficult procedures much simpler. Of even more importance, however, is the fact that the use of surgical staples significantly reduces the time required for most procedures and, therefore, reduces the length of time for which the patient must be maintained under anesthetic.

Many types of surgical stapling instruments have been devised for many different procedures. The present invention is directed to a linear surgical stapling instrument. This is an instrument which, on a single actuation, simultaneously implants and forms at least one rectilinear row of surgical staples. Such instruments are used on many different organs and tissues, such as the lung, the esophagus, the stomach, the duodenum, and throughout the intestinal tract.

In its earliest form, the linear surgical stapling instrument was a permanent, multi-use instrument, and the surgical staples were manually loaded into the instrument one-by-one. An exemplary surgical stapling instrument of this type is taught in U.S. Pat. No. 3,080,564. While such instruments performed well, they were, in general, complex in construction, expensive to manufacture, heavy, bulky and difficult both to load with surgical staples and to clean and sterilize after each use.

A significant improvement in the linear surgical stapling instrument came about with the provision of pre-sterilized, disposable loading units or staple cartridges. U.S. Pat. Nos. 3,275,211 and 3,589,589 are exemplary of those relating to permanent, multi-use, linear instruments having replaceable staple cartridges. While this improvement significantly reduced the time previously required for hand-loading of the staples, the basic instrument still had to be disassembled, cleaned, reassembled and sterilized for each procedure, and frequently required additional maintenance and adjustment. Also, if more than one load of staples was required in a given procedure, the cartridge had to be replaced each time, as it contained only a single load.

Even more recently, in view of rising hospital costs, there has been an ever increasing interest in disposable surgical stapling instruments, to eliminate as much work as possible (i.e., disassembling, cleaning, reassembling, sterilization and the like) and to be more efficient, while at the same time not having to compromise the surgical procedures.

Such a disposable linear surgical stapling instrument is taught, for example, in U.S. Pat. No. 4,527,724 This instrument, simple in construction and relatively inexpensive to manufacture, is characterized by a working gap or range of distances between the instrument anvil and the cartridge over which a single size staple can be properly implanted and formed. The proper and desired setting of the instrument, within the working gap, is easily accomplished through simple manipulation of an adjustment knob at the rear of the instrument with indicator means on each side of the instrument to clearly show when the distance between the anvil and the cartridge is within the working gap. In addition, the gap to which the instrument is set can fall anywhere within the confines of the working gap of the instrument. The instrument is provided with an alignment and retaining pin, shiftable to an operable position wherein alignment between the anvil and the staple cartridge is ensured, and wherein tissue to be sutured, located between these elements, is retained therebetween. The instrument is provided with a lockout device which precludes rotation of the adjustment knob to secure the desired gap unless the alignment and retaining pin has been shifted to its operative position. The instrument is also provided with a novel trigger safety which will disable the trigger until the movable jaw of the instrument has been shifted to a position near the working gap.

For purposes of economy and simplicity, much of the instrument is made of appropriate plastic material, while most of the major load-bearing elements of the instrument are metallic. The instrument is so designed that the staple driver is coupled to the trigger at all times. As a result of this, the driver is not free floating and cannot accidentally dislodge or discharge the surgical staples during shipping and handling prior to use of the instrument in the operating room.

As indicated above, linear surgical stapling instruments (whether they be permanent, reusable instruments or disposable, single-use instruments) are characterized by the fact that they simultaneously form and implant at least one rectilinear row of surgical staples. In fact, the most commonly encountered linear surgical stapling instrument simultaneously forms and implants two rectilinear rows of surgical staples, with the surgical staples of one row being offset or staggered with respect to the surgical staples of the other row. This assures reliable suturing of the tissue to be joined together.

It has been found that it would be a matter of great convenience to the surgeon if the staple cartridge would contain more than one load of surgical staples. The word "load" used here and hereinafter refers to that number of staples required to make up the single or double row of staples implanted when the surgical stapling instrument is actuated. This would enable the surgeon to perform two or more suturing procedures before changing cartridges in a permanent or disposable multiple-use instrument or changing instruments in the case of a disposable instrument.

As a consequence, the present invention is directed to a multiple-load cartridge assembly for a linear surgical stapling instrument. Depending upon the materials from which the elements of the cartridge of the present invention are made and the manner in which they are assembled, the cartridge may be provided in a number of forms. For example, the cartridge can constitute a reusable, refillable cartridge to be used with a permanent, nondisposable linear surgical stapling instrument. The cartridge can be a replaceable and disposable cartridge for a permanent instrument. The cartridge can be a reusable, refillable cartridge for a disposable instrument. The cartridge can be a replaceable and disposable cartridge for a disposable instrument. Finally, the cartridge can constitute a permanent part of a disposable instrument, the instrument and cartridge being disposed of when the cartridge is empty.

DISCLOSURE OF THE INVENTION

According to the invention, there is provided a multiple-load cartridge assembly for use with a linear surgical stapling instrument of the type which, when actuated, simultaneously implants at least one row of staples in the tissue of a patient, and forms or clinches the staples of the row against the instrument anvil.

In its simplest form, the cartridge assembly comprises a cartridge having at least one row of staple-containing forming pockets and a driver having a plurality of blades equal in number to the number of forming pockets. The driver blades are configured to drive the staples from the forming pockets through the tissue to be sutured and against the tool anvil to be clinched, when the surgical stapling instrument is actuated. The cartridge also has a plurality of storage pockets, equal in number to the forming pockets and each containing one staple. After the first actuation of the surgical stapling instrument, an indexing mechanism, mounted within the cartridge, shifts the staple in each storage pocket into the adjacent forming pocket, to reload the forming pockets for another actuation of the surgical stapling instrument. An interlock may be located within the cartridge and prevents actuation of the indexing mechanism until the forming pockets have been cleared of the first staple load. In this way, correct sequential operation of the cartridge is assured and jamming of the cartridge is precluded.

In a second embodiment of the invention, each storage pocket may contain a plurality of surgical staples arranged one behind the other in a row extending perpendicular to the driver. Upon each actuation of the driver and return thereof to its retracted position, an indexing member shifts a staple from each storage pocket to each forming pocket. A third embodiment is similar to the second embodiment with the exception that each row of staples in each storage pocket extends diagonally with respect to the driver.

In a fourth embodiment, a staging pocket is located between each holding pocket and each forming pocket. An indexing mechanism is provided to shift a staple from the storage pocket to the staging pocket. A second indexing mechanism is provided to shift a staple from the staging pocket to the forming pocket. In yet another embodiment having a storage pocket and a staging pocket for each forming pocket, the staples are stacked one above the other in the storage pocket and are fed automatically by spring means or the like into the staging pocket. An indexing mechanism is provided to shift a staple from the staging pocket to the forming pocket.

To demonstrate the application of the present invention to an existing linear surgical stapling instrument, there is taught herein an embodiment of the cartridge of the present invention constituting a permanent part of a disposable linear surgical stapling instrument of the type described in the above noted U.S. Pat. No. 4,527,724. The cartridge contains two loads of staples and the linear surgical stapling instrument is capable of two actuations, forming and implanting two staggered rows of surgical staples with each actuation of the instrument. Thereafter, the instrument and its cartridge are disposed of. The cartridge assembly comprises a cartridge having two staggered parallel rows of forming pockets and a storage pocket for each forming pocket. Each forming pocket and each storage pocket contains one surgical staple. A driver is provided having a driving blade for each forming pocket. The cartridge assembly is provided with a casing which is mounted on the cartridge with a support plate therebetween. The driver is mounted within the casing, with its driving blades extending through the support plate and into the cartridge.

A slider is provided for each row of storage pockets. The sliders are actuated by a manual indexing button slidably mounted in the casing. When the button is manually shifted, it will shift the sliders which, in turn, will index the staples in the storage pockets into their respective forming pockets. A safety is provided to preclude actuation of the indexing button until the linear surgical stapling instrument has been once actuated to clear the forming pockets of their first staple load. Thereafter, when the driver is returned to its normal retracted position, the indexing button can be shoved inwardly with respect to the casing, causing the sliders to shift the staples in the storage pockets into their respective forming pockets, providing a second load of staples in the forming pockets and enabling a second actuation of the instrument.

In another embodiment of the invention, one or more sets of storage pockets, each containing one staple, are provided and are arranged identically to the forming pockets. The first set of forming pockets and all the sets of storage pockets are movable with respect to the instrument centerline through any appropriate path of travel (rectilinear, arcuate, etc). After the first actuation of the instrument, which clears the first forming pockets, and when the driver is retracted, the at least one more set of storage pockets can be moved into alignment between the driver and the anvil, displacing the first set of empty forming pockets. These storage pockets thus become forming pockets to allow for at least another actuation of the instrument.

BRIEF DESCRIPTION OF THE DRAWINGS

FIGS. 1–4 are diagrammatic representations, partly in cross-section, of a double-load embodiment of the cartridge assembly of the present invention, illustrating its sequential operation.

FIGS. 13–16 are diagrammatic representations, partly in cross-section, of another embodiment having a staging pocket between each storage pocket and forming pocket, and illustrating the sequence of operation thereof.

FIGS. 17–20 are diagrammatic representations, partly in cross-section, illustrating an embodiment of the present invention similar to that of FIGS. 13–16, but having a vertical stack of staples in each storage pocket and automatic means to feed staples from each storage pocket to each staging pocket, and further illustrating the mode of operation of this embodiment.

FIG. 23 is a fragmentary perspective view of the cartridge of the cartridge assembly.

FIG. 24 is a plan view of the cartridge.

FIG. 24A is a fragmentary plan view of the cartridge illustrating one slot comprising a forming pocket and a storage pocket.

FIG. 25 is a side elevational view of the cartridge

FIG. 26 is an end elevational view of the cartridge, as seen from the left of FIG. 25.

FIG. 27 is an end elevational view of the cartridge, as seen from the right of FIG. 25.

FIG. 28 is a cross-sectional view taken along section line 28-28 of FIG. 24.

FIG. 32 is a bottom view of the cartridge of the present invention.

FIG. 33 is a bottom view of the driver of the present invention.

FIG. 34 is a side elevational view of the driver of FIG. 33.

FIG. 35 is an end elevational view of the driver of FIGS. 33 and 34.

FIG. 41 is a top plan view of the support plate of the present invention.

FIG. 42 is a side elevational view of the support plate. FIG. 43 is an end elevational view of the support plate, as seen from the left of FIG. 42. FIG. 44 is an end elevational view of the support plate, as seen from the right of FIG. 42. FIG. 45 is a plan view of the cartridge, illustrating the sliders and the support plate mounted in place. FIG. 46 is a plan view of the casing of the present invention. FIG. 47 is a side elevational view of the casing. FIG. 48 is an end elevational view of the casing, as viewed from the right of FIG. 47. FIG. 49 is an end elevational view of the casing, as viewed from the left of FIG. 47. FIG. 50 is a bottom view of the casing. FIG. 51 is a cross-sectional view, taken along section line 51—51 of FIG. 46. FIG. 58 is a fragmentary plan view of the cartridge, with the indexing button mounted therein. FIG. 59 is a fragmentary elevational side view of the cartridge and casing with the indexing button mounted therein. FIG. 60 is a plan view of the safety of the present invention. FIG. 61 is an end elevational view of the safety.

FIG. 62 is a side elevational view of the safety.

FIG. 63 is a fragmentary, cross-sectional view taken along section line 63—63 of FIG. 45 and showing the casing, the driver and the handle plates.

FIG. 64 is a fragmentary, cross-sectional view taken along section line 64—64 of FIG. 45 and showing the casing and the indexing button.

DETAILED DESCRIPTION OF THE INVENTION

Figure 4:
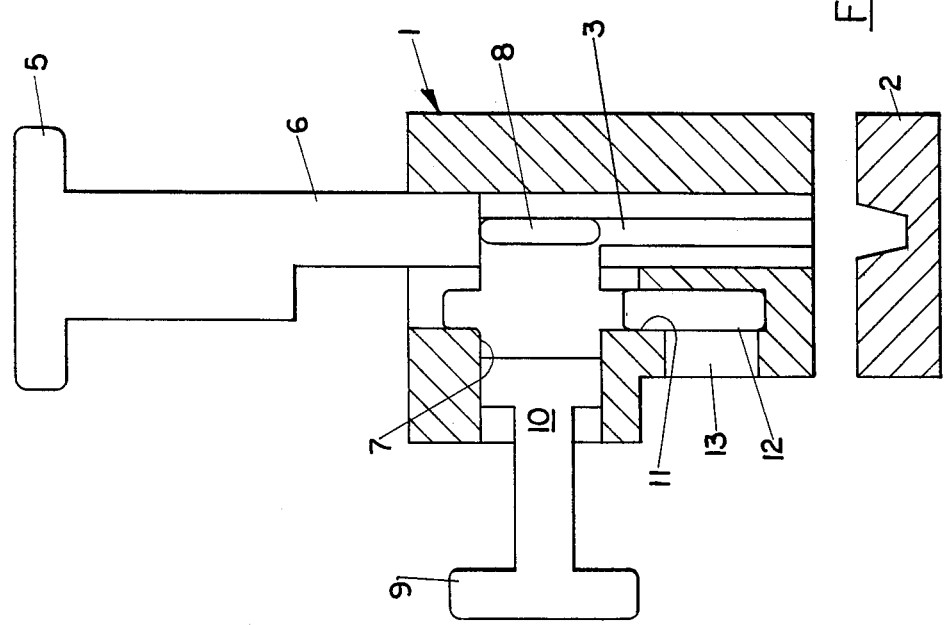

FIGS. 1-20 are simplified diagrammatic representations illustrating the basic concepts of the cartridge assembly of the present invention.

Reference is first made to FIG. 1, wherein a cartridge assembly is generally indicated at 1. The anvil of a linear surgical stapling instrument is diagrammatically indicated at 2. The cartridge 1 is provided with a plurality of forming pockets, one of which is shown at 3. A staple 4 is located within the forming pocket 3. It will be understood that, as viewed in FIG. 1, the forming pockets 3 will be located one behind the other in a linear row. Each will contain a staple equivalent to staple 4, so that the staples, themselves, will be arranged in a linear row.

A staple driver is shown at 5. The staple driver is provided with a blade for each forming pocket, the blades being slidably mounted in their respective forming pockets. The blade for forming pocket 3 is shown at 6.

A storage pocket 7 communicates with the upper end of forming pocket 3. It will be understood that there will be a similar storage pocket for each forming pocket. Storage pocket 7 contains a staple 8, as will all of the other storage pockets. An indexing mechanism is indicated at 9. In this diagrammatic representation, the indexing mechanism is illustrated as having a plunger-like element for each storage pocket. The plunger-like element of indexing mechanism 9 for storage pocket 7 is shown at 10.

To complete the structure, a vertical slot is shown at 11. The vertical slot 11 contains a safety 12 slidably mounted therein. There may be a vertical slot 11 and safety 12 for each set of forming pockets and storage pockets. Alternatively, the slot 11 may run longitudinally throughout the length of cartridge assembly 1 with the safety 12 also extending the full length of the cartridge assembly 1. A window 13 may be provided, communicating with the lower end of slot 11.

FIG. 1 illustrates the cartridge assembly 1 in its initial fully loaded condition. It will be understood that the cartridge assembly 1 will be mounted on a linear surgical stapling instrument (not shown). The operation of cartridge assembly 1 will be described in terms of forming pocket 3, storage pocket 7 and staples 4 and 8. It will be understood that precisely the same things will occur in all of the forming pockets and storage pockets.

When the linear surgical stapling instrument (not shown) is actuated for a first time, the driver 5 will be shifted downwardly to the position shown in FIG. 2. This will drive staple 4 through tissue (not shown) located between the cartridge assembly 1 and anvil 2, and will cause the staple 4 to be formed by anvil 2. At the same time, the safety 12, which when in the position shown in FIG. 1 precluded actuation of index mechanism 9, is shifted downwardly in slot 11 by driver 5.

Figure 3:
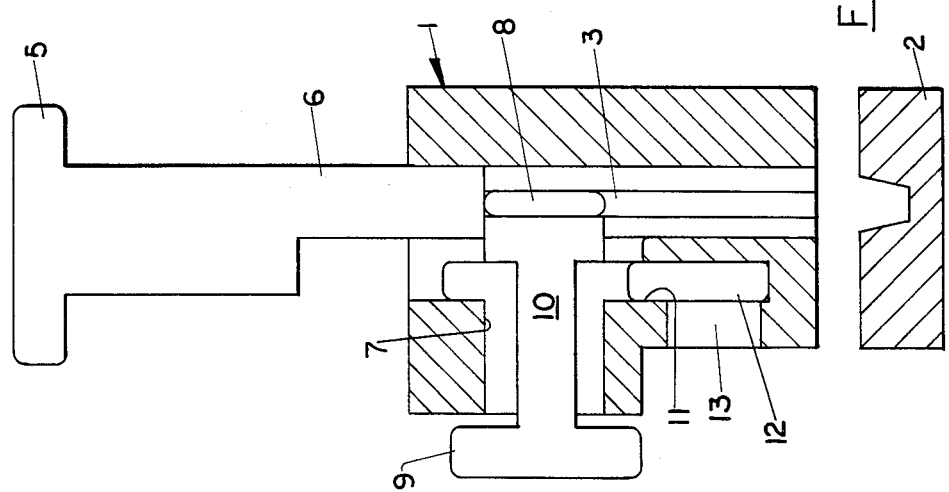

After the first actuation of the linear surgical stapling instrument, the driver 5 is withdrawn to its normal retracted position. With the safety 12 located in the bottom of slot 11, the indexing mechanism 9 is free to be actuated, shoving staple 8 from storage pocket 7 into forming pocket 3, as illustrated in FIG. 3. When the indexing mechanism 9 is returned to its normal retracted position, as shown in FIG. 4, the staple 8 is free to be implanted and formed by a second actuation of the linear surgical stapling instrument, in the same manner described with respect to staple 4 in FIG. 2.

The window 13 provides a visual indication to the surgeon that the cartridge assembly 1 is ready for the first actuation of the linear surgical stapling instrument or the second actuation of the linear surgical stapling instrument. This can be accomplished in several ways. The inside of slot 11 may be provided with one color and the safety with another. Similarly, the inside surface of slot 11 may be provided with indicia viewable through window 13 and the safety 12 may be provided with additional indicia viewable through window 13. Both colors and indicia, viewable through window 13, can be used. The cartridge assembly 1 of FIGS. 1-4 constitutes a simple example of a two-load cartridge assembly.

An exemplary multiple-load cartridge assembly is illustrated diagrammatically in FIGS. 5-8. In this instance, the cartridge assembly is generally indicated at 14 and is shown in cross-section through one side of the cartridge (i.e., one set of forming pockets and storage pockets). A forming pocket is shown at 15 and its respective storage pocket is shown at 16. A driver 17, similar to driver 5 of FIG. 1, is shown, together with its blade 18 for forming pocket 15. An indexing mechanism 19, similar to indexing mechanism 9 of FIG. 1 is shown, provided with its plunger-like portion 20 for storage pocket 16. The anvil of the linear surgical stapling instrument (not shown) to which cartridge assembly 14 is attached is indicated at 21.

Figure 5:
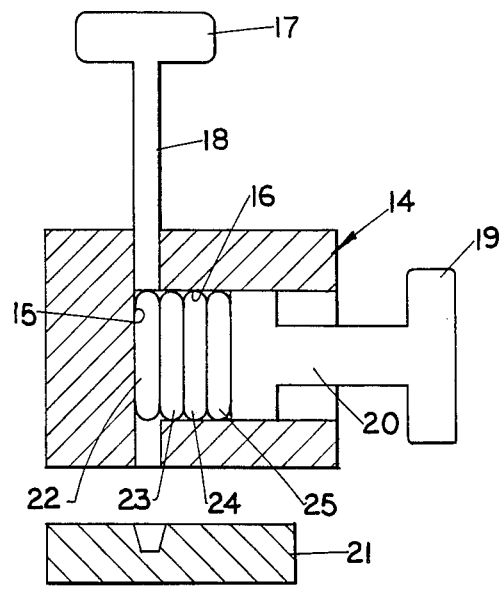
FIGS. 5–8 are diagrammatic representations, partly in cross-section, of a multiple-load embodiment of the cartridge assembly of the present invention, illustrating its sequential operation.
Figure 6:
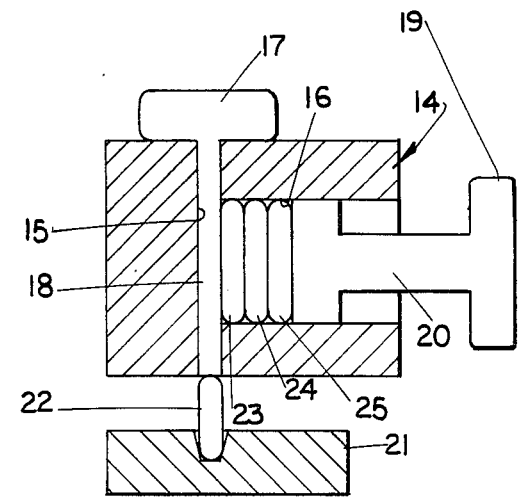

FIG. 5 illustrates the cartridge assembly 14 in its initial unfired condition. A staple 22 is located in forming pocket 15 and three additional staples 23, 24 and 25 are located within storage pocket 16. FIG. 6 illustrates the cartridge assembly 14 after the linear surgical stapling instrument (not shown) has been actuated for a first time. This results in driver 17 and its blade 18 forcing surgical staple 22 through tissue (not shown) located between cartridge assembly 14 and anvil 21, and clinching the surgical staple 22 against anvil 21. It will be understood that all of the other staples (not shown) in all of the other forming pockets (not shown) will be similarly implanted and formed.

Figure 7:
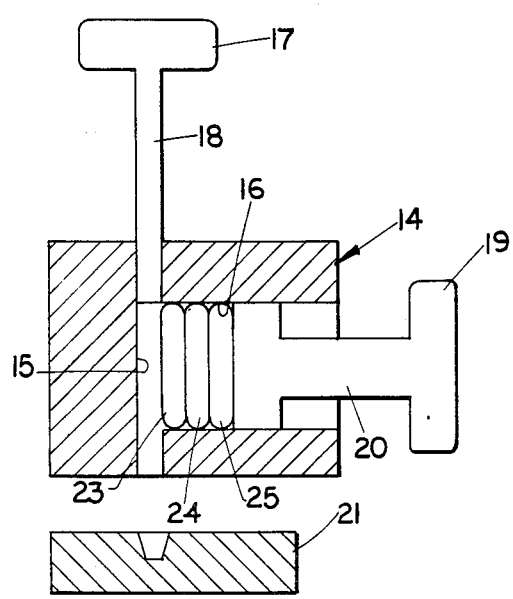
Figure 8:
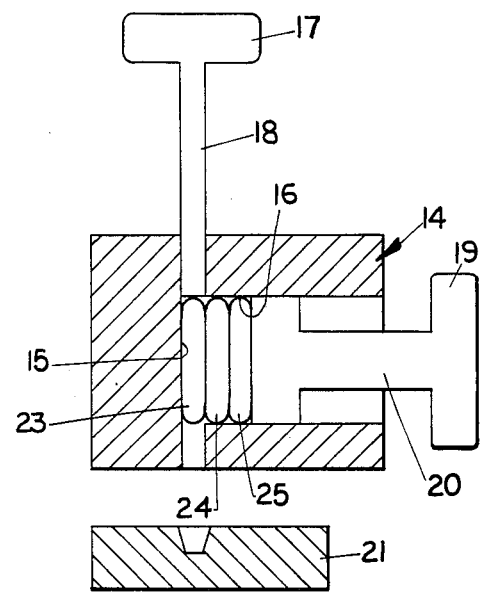
Figures 9, 10:
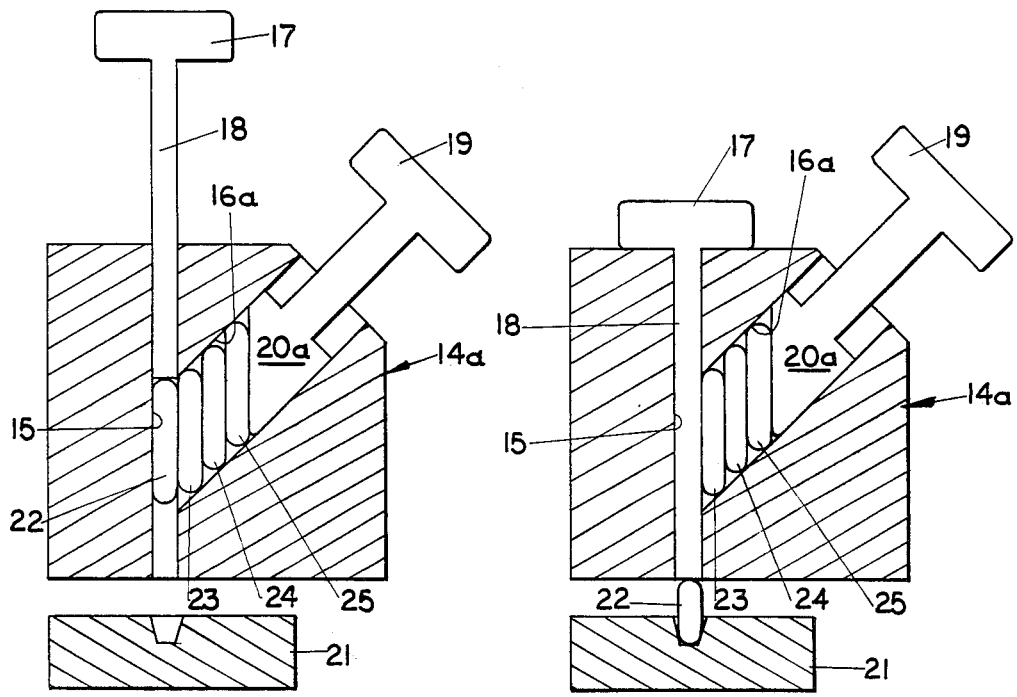
FIGS. 9–12 are diagrammatic representations, partly in cross-section, illustrating an embodiment similar to that of FIGS. 5–8, with the row of staples in each storage pocket extending diagonally with respect to the driver.
Figures 11, 12:
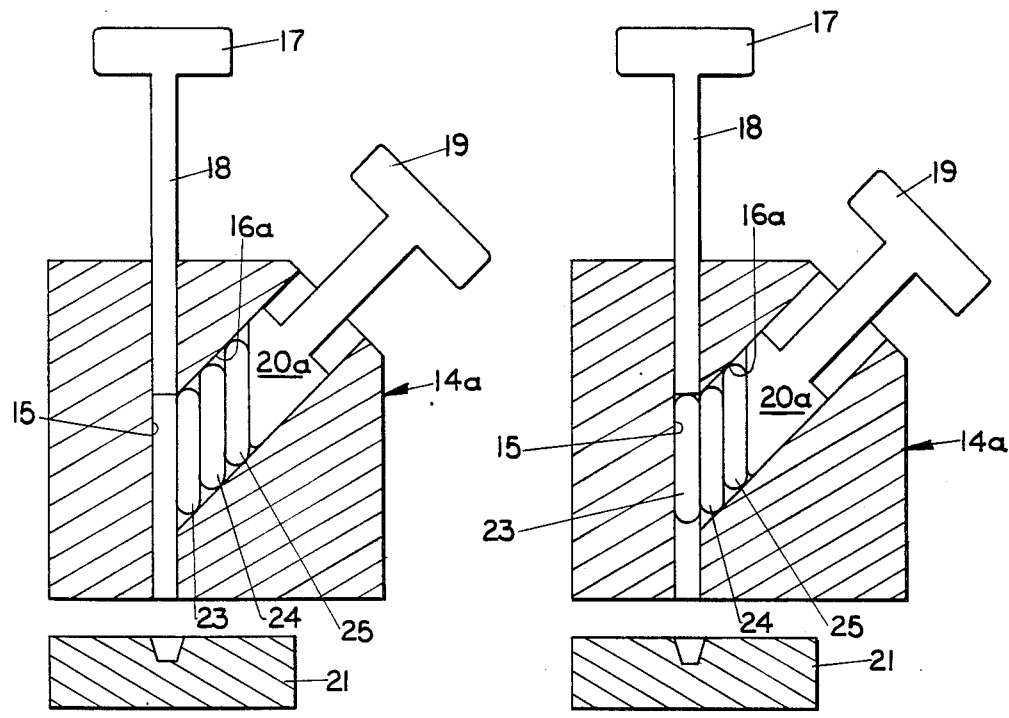

At the end of the first cycle of the linear surgical stapling instrument, the driver 17 will be returned to its normal retracted position, as shown in FIG. 7. At this point, the indexing mechanism 19 will shift all of the next staples 23 in each of the storage pockets 16 into their respective forming pockets 15. This is shown in FIG. 8, wherein the first staple 23 of storage pocket 16 has been shifted into forming pocket 15. The linear surgical stapling instrument (not shown) can be actuated for a second time. This will result in implanting and forming or clinching of staple 23. This same procedure can be repeated through the implanting and clinching of staple 25, at which point the cartridge assembly 14 is empty and may be refilled or disposed of, depending upon whether it is a refillable and reusable cartridge assembly or a disposable cartridge assembly.

FIGS. 9-12 diagrammatically illustrate another embodiment of cartridge assembly similar to that shown in FIGS. 5-8. Like parts have been given like index numerals. Cartridge assembly 14a differs from cartridge assembly 14 of FIGS. 5-8 only in that the storage pocket 16a lies at an angle to the forming pocket 15. The plunger-like portion 20a of indexing mechanism 19 is appropriately configured to advance staples 23-25 in the storage pocket 16a. It will apparent from FIGS. 9-12 that the operation of cartridge assembly 14a is substantially identical to that described with respect to the cartridge assembly 14 of FIGS. 5-8. FIGS. 9-12 illustrate that variations can be made in the geometry and/or motions within the cartridge assembly of the present invention.

Another embodiment of the cartridge assembly of the present invention is diagrammatically illustrated in FIGS. 13-16. Again, it will be understood that the cartridge assembly, generally indicated at 26, will be attached to a linear surgical stapling instrument (not shown) having an anvil 27. Again, the views 13-16 are cross-sectional views through one side of the cartridge, illustrating one of a plurality of forming and storage pockets. The forming pocket is shown at 28. The storage pocket is shown at 29.

A driver 30, equivalent to driver 5 of FIG. 1, is provided having a blade for each forming pocket. The blade for forming pocket 28 is shown at 31. A first indexing mechanism 32 is provided with a plunger-like portion for each storage pocket. The plunger-like portion for storage pocket 29 is shown at 33.

The embodiment of FIGS. 13-16 differs from the previously described multiple-load cartridge assemblies in that a staging pocket is provided between each storage pocket and forming pocket. The staging pocket between forming pocket 28 and storage pocket 29 is shown at 34.

The indexing mechanism 32 comprises a first indexing mechanism adapted to shift a staple from storage pocket 29 to staging pocket 34. A second indexing mechanism is provided and is indicated at 35. The purpose of the second indexing mechanism 35 is to shift a staple from the staging pocket 34 to forming pocket 28. As in the case of the first indexing mechanism 32, indexing mechanism 35 will have a plunger-like portion 36 for each staging pocket of the cartridge assembly 26.

It will be noted in FIG. 13 that a first staple 37 is located in forming pocket 28. Storage pocket 29 contains three additional staples 38, 39 and 40. Storage pocket 29 also contains a pusher 41 actuated by a compression spring 42.

In FIG. 13, the cartridge assembly 26 is shown in its initial, fully loaded condition. A first actuation of the linear surgical stapling instrument (not shown) will cause driver 30 to force staple 28 through tissue (not shown) located between the cartridge assembly 26 and the anvil 27 and to clinch staple 28 against anvil 27. At the same time, the first indexing mechanism 32 shifts the first staple 38 of storage pocket 29 into staging pocket 34. In fact, the first indexing mechanism 32 could be actuated by driver 30. To this end, driver 30 is shown in FIG. 13 as having a lug (shown in broken lines) 30a overlying first indexing mechanism 32, which will actuate indexing mechanism 32 when driver 30 is actuated.

Figure 16:
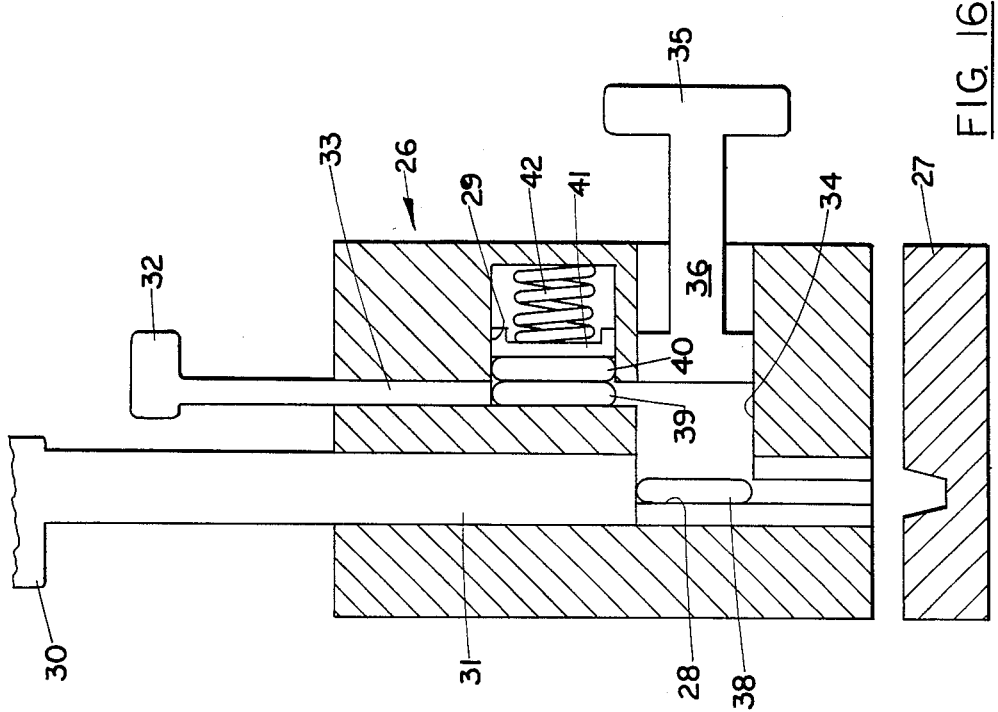
Figure 15:
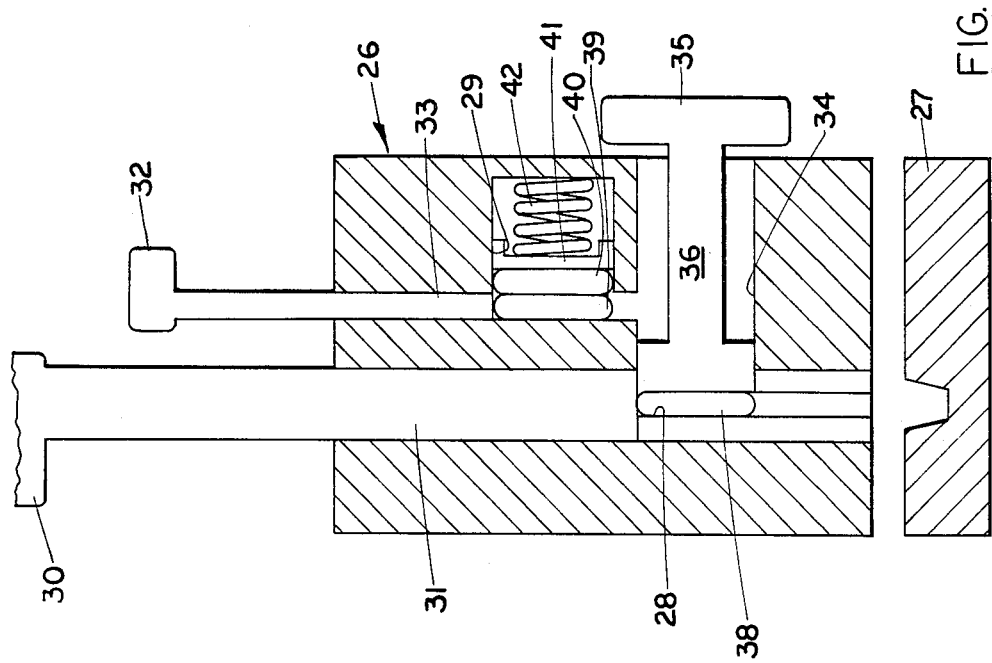

After the first actuation of the linear surgical stapling instrument, driver 30 is returned to its normal retracted position, as shown in FIG. 15. At the same time, first indexing mechanism 32 is returned to its normal retracted position. This enables the pusher 41 and coil spring 42 to shift the next surgical staple 39 beneath the first indexing mechanism 32. At this stage, the second indexing mechanism 35 can be used to shift the second staple 38 from the staging pocket 34 to forming pocket 28. Thereafter, the second indexing mechanism 35 is returned to its normal position as shown in FIG. 16 and the cartridge assembly is ready for the next actuation of the linear surgical stapling instrument. This series of steps may be continued until the last staple 40 of cartridge assembly 26 has been implanted and formed. Another embodiment of the present invention is illustrated in FIGS. 17-20. The embodiment of FIGS. 17-20 is similar to that of FIGS. 13-16 and again demonstrates how variations in geometry and/or motions within the cartridge assembly can be made.

Turning first to FIG. 17, the cartridge assembly is generally indicated at 43 and is intended to be affixed to a linear surgical stapling instrument (not shown) having an anvil 44. As in the case of the embodiment of FIGS. 13-16, the cartridge assembly 43 is provided with a plurality of forming pockets, staging pockets and storage pockets. In FIG. 17, one set of these pockets is illustrated. The forming pocket is shown at 45. The staging pocket is indicated at 46 and the storage pocket is shown at 47. The cartridge assembly 43 is provided with a driver 48 having a blade for each forming pocket. The blade for forming pocket 45 is shown at 49. As in all of the embodiments, the cartridge assembly 43 aligns the driver with respect to anvil 44. An indexing mechanism 50 is provided having a plunger-like portion for each staging pocket. The plunger-like portion for staging pocket 46 is shown at 51. The indexing mechanism 50 is equivalent to indexing mechanism 35 of FIG. 13. In FIG. 17, a first staple is shown at 52 in forming pocket 45. A second staple is shown at 53 in staging pocket 46 and third and fourth staples are shown at 54 and 55 in storage pocket 47.

In the embodiment of FIG. 17, the storage pockets differ from those of the embodiment of FIG. 13 in several respects. First of all, the storage pocket 47 is oriented parallel to the blade 49 of driver 48. The surgical staples 54 and 55 are stacked in storage pocket 47 one above the other. The storage pocket is provided with a pusher 56 actuated by a compression spring 57 and guided in guideways 58 and 59. Thus, pusher 56 and compression spring 57 automatically feed surgical staples from the storage pocket 47 to staging pocket 46 without the necessity of an additional indexing mechanism equivalent to indexing mechanism 32 of FIG. 13.

FIG. 17 illustrates the cartridge assembly 43 in its initial fully loaded condition, ready for the linear surgical stapling instrument (not shown) to be actuated for a first time. Upon actuation of the linear surgical stapling instrument, the driver 48 forces the staple 52 in forming pocket 45 to pass through tissue (not shown), located between the cartridge assembly 43 and the anvil 44, and to be clinched by the anvil 44. This is shown in FIG. 18.

After the first actuation of the linear surgical stapling instrument, the driver 48 is returned to its initial retracted position and indexing mechanism 50 may be used to shift the second staple 53 from staging pocket 46 into forming pocket 45. This is shown in FIG. 19. Thereafter, the indexing mechanism 50 is returned to its normal position as shown in FIG. 20 and the third staple 54 is shifted from storage pocket 47 to holding pocket 46 by pusher 56 and compression spring 57. The cartridge assembly 43 is now ready for a second actuation of the linear surgical stapling instrument. These sequential operations can be continued until the last staple 55 of cartridge assembly 43 has been formed and implanted.

In all of the embodiments of FIGS. 5-20, safety interlocks and load counting means have been omitted for purposes of clarity. It will be understood, however, that such elements could and preferably would be provided with each embodiment. It will be understood by one skilled in the art that efficient design of the cartridge design would allow for single inputs from the surgeon via the linear surgical stapling instrument to result in several motions within the cartridge. For example, the forward stroke of the driver could not only form staples, but could also transfer staples from the storage pockets to the staging pockets, as described with respect to the embodiment of FIGS. 13-16. Similarly, the driver could be spring loaded so that it returns upon release, and in so doing, staples could be shifted from the storage pockets (or staging pockets if present) to the forming pockets. It could be within the scope of the invention to provide some form of stored energy source, such as a battery or compressed gas, to partially or fully operate the cartridge assembly.

As has been disclosed above, the geometry and/or the motions within the cartridge assembly can be widely varied. The use of staging pockets, as is evident from the above, is optional.

In all of the embodiments of FIGS. 1-20, the driver may or may not be a part of the multiple load cartridge assembly, as desired. Similarly, the anvil could be a part of the cartridge assembly, or not, as desired.

As indicated above, the cartridge assembly of the present invention may be permanent and refillable or it may be a single-use, disposable assembly. For purposes of a complete disclosure, the teachings of the present invention will now be described as applied to an actual linear surgical stapling instrument. While not intended to be so limited, for purposes of an exemplary showing the cartridge assembly of the present invention will be described in its application as a permanent part of a disposable linear surgical stapling instrument of the type taught in the above-identified U.S. Pat. No. 4,527,724. The teachings of this co-pending application are incorporated by reference herein, in their entirety.

Figure 21:
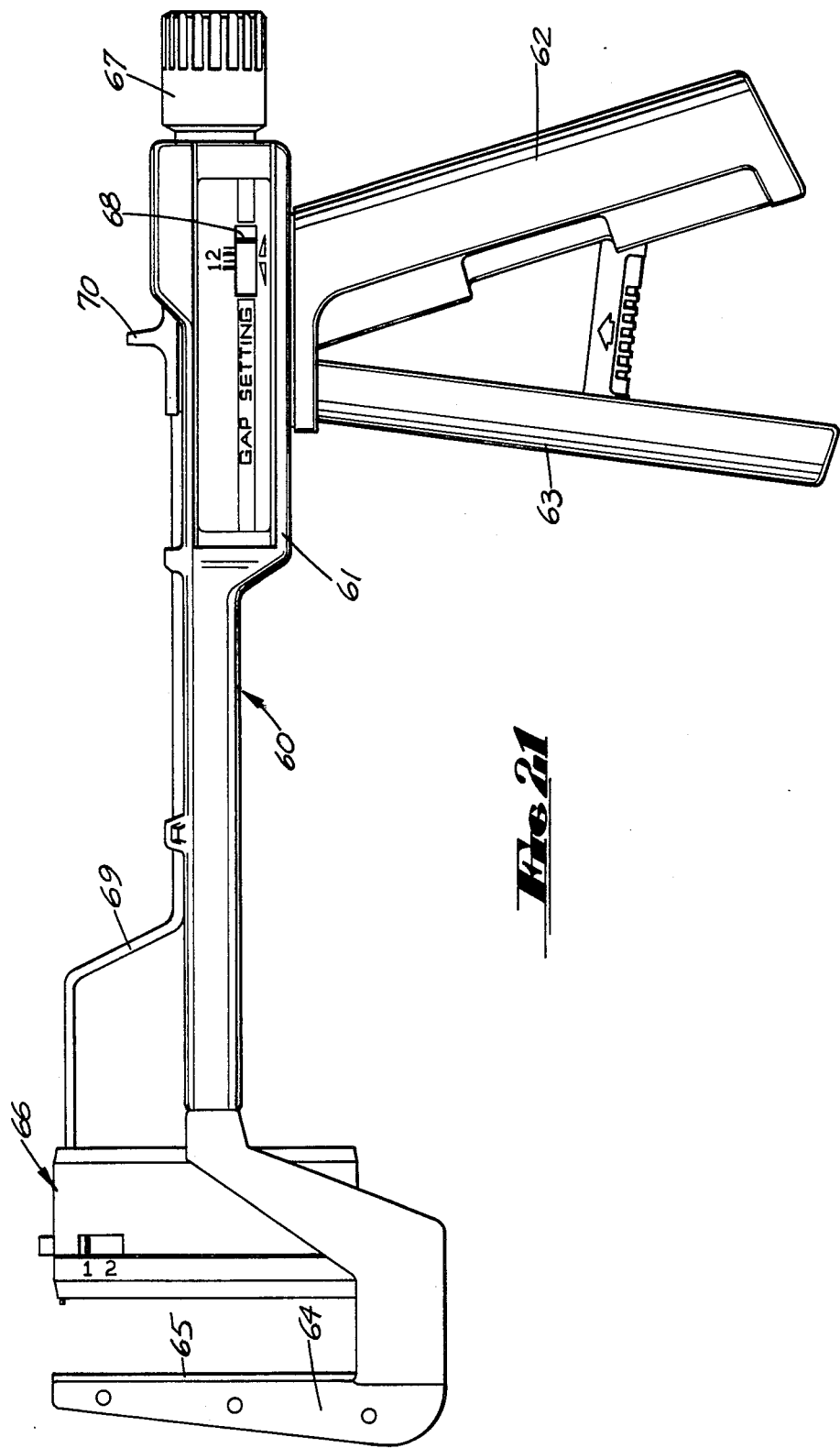
FIG. 21 is a side elevational view of an exemplary linear surgical stapling instrument provided with the cartridge assembly of the present invention.

A disposable linear surgical stapling instrument of the type contemplated is illustrated in FIG. 21 and is generally indicated at 60. Briefly, the instrument 60 comprises a body 61 having a handle 62 and a trigger assembly 63. The instrument is provided at its forward end with a fixed jaw 64, supporting an anvil 65. The instrument 60 is also provided with a movable jaw comprising the cartridge assembly of the present invention and generally indicated at 66. The movable jaw 66 is shiftably mounted on the body 61 and is operatively connected to the handle and trigger assembly 62-63.

An adjustment bolt (not shown) is slidably mounted within the body 61 and is shiftable forwardly and rearwardly therein. An adjustment knob 67 is rotatably mounted at the rearward end of the body 61. The adjustment knob is operatively connected to the bolt to cause the bolt to shift forwardly and rearwardly within body 61.

When the adjustment bolt is shifted forwardly within the instrument body 61, by means of the adjustment knob 67, the bolt moves the handle and trigger assembly 62–63 forwardly and causes the movable jaw or cartridge assembly 66 to approach the fixed jaw 64. In other words, the cartridge assembly 66 approaches the anvil 65. A staple driver (not shown) is located in association with cart ridge assembly 66 and is connected to and is shiftable by trigger 63 to drive staples from the cartridge assembly, through tissue (not shown) to be sutured (located between the cartridge assembly 66 and the anvil 65), and against the anvil 65. The anvil has a plurality of anvil pockets (not shown) configured to clinch the staples over a range of distances between the anvil 65 and the cartridge assembly 66, constituting the "working gap" of the instrument. The adjustment bolt also actuates indicator means 68 located on each side of the instrument 60, clearly showing when the working gap has been achieved between the anvil 65 and the cartridge assembly 66. The indicator means 68 is such that it will assist the surgeon in adjusting the distance between the anvil 65 and the cartridge assembly 66 within the working gap of instrument 60.

An alignment pin 69 is shiftably mounted on the instrument body 61, extending through cartridge assembly 66. The alignment pin is manually shiftable by handle means 70 from its retracted position shown in FIG. 21 to an operative position wherein it also extends into the fixed jaw 64. In this way, the alignment pin 69 not only assures that the anvil 65 and cartridge assembly 66 are properly oriented with respect to each other, but also traps the tissue (not shown) to be sutured between the anvil 65 and the cartridge assembly 66.

Figure 22:
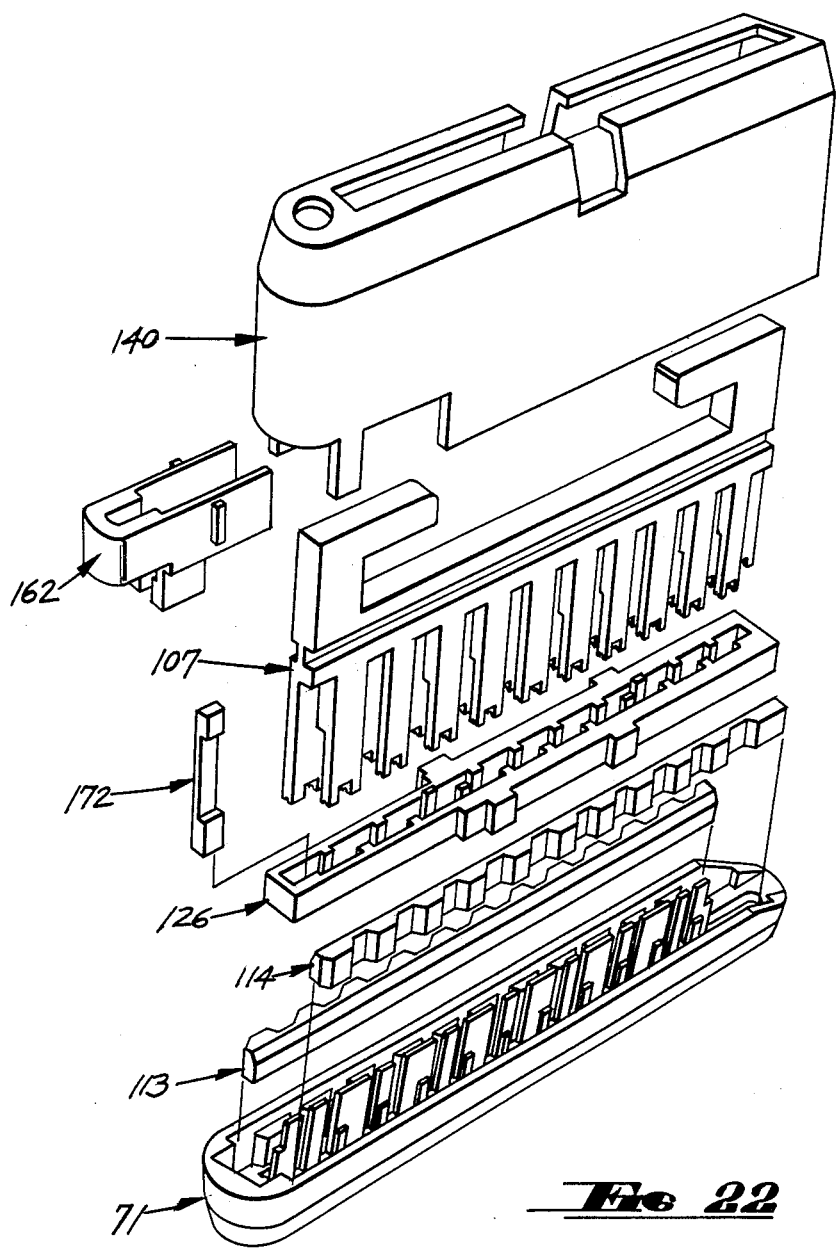
FIG. 22 is an exploded perspective view of the cartridge assembly of FIG. 21.

FIG. 22 is an exploded view of the cartridge assembly 66 of FIG. 21. The cartridge assembly 66 is made up of a cartridge 71, a driver 107, first and second sliders 113 and 114, a support plate 126, an indexing button 162, a casing 140 and a safety 172. Each of these elements will be described in detail.

The cartridge 71 is shown in FIGS. 23 through 32, wherein like parts have been given like index numerals. Cartridge 71 comprises an integral, one-piece molded plastic member comprising an elongated body 72, having a bottom 73 and an upstanding surrounding wall or flange 74 extending along its longitudinal edges and about its end 75. At its end 76, the wall 74 slopes downwardly to the bottom 73, as at 77 and 78.

Along one of its longitudinal flights, the wall 74 has, on its inside surface, a plurality of integral, inwardly extending cam members 79. In similar fashion, along the other of its longitudinal flights, the wall 74 has, on its inside surface, a second series of integral cam members 80. As will be most apparent from FIGS. 24 and 29, the cam members 79 are substantially identical, as are the cam members 80. Additionally, the cam members 79 and 80 are substantially identical. It is to be noted, however, that the cam members 80 are staggered with respect to the cam members 79 and, as a result, the cam members 80 are one less in number than the cam members 79.

The number of cam members 79 and 80 is not a limitation on the present invention. For convenience, the cam members 79 an 80 have been shown equal in number to the slots forming the storage and forming pockets described hereinafter.

Figure 29:
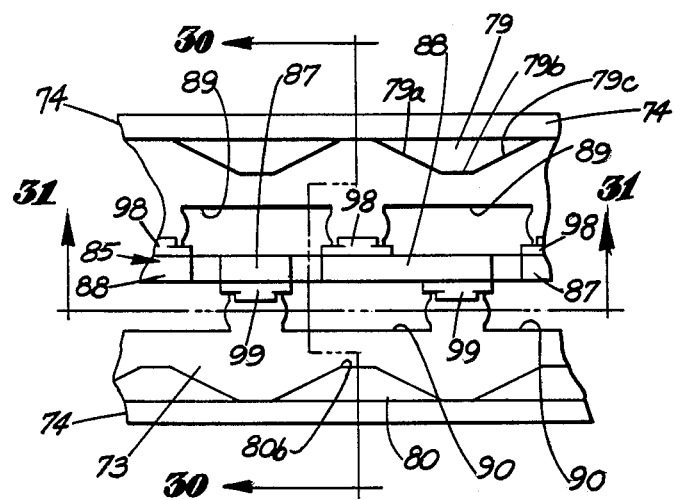
FIG. 29 is an enlarged, fragmentary, simplified plan view of the cartridge.

Reference is made to FIG. 29. It will be noted that each cam member 79 has a first planar surface 79a lying at an angle to wall 74 and extending away therefrom, a second surface 79b parallel to the inside surface of wall 74 and a third surface 79c extending from surface 79b to the inside surface of wall 74. Each cam member 80 has wall surfaces 80a, 80b and 80c, equivalent to the wall surfaces 79a through 79c of cam members 79. The purpose of cam members 79 and 80 will be apparent hereinafter.

Near the end 75 of cartridge 71, the bottom 73 has a perforation 81. The perforation 81 is adapted to accommodate alignment and retaining pin 69 (see FIG. 21). Near its other end 76, the bottom 73 of cartridge 71 has an elongated slot 82. The slot 82 is adapted to accommodate the shank of the instrument pilot 82a (see FIG. 45). The pilot 82a comprises a part of fixed jaw 64 and has a shank lying at 90° to anvil 65 and passing through cartridge 71 to render the cartridge captive and slidable with respect to instrument 60. The pilot 82a is fully described in the above noted co-pending application.

The outside surface of what has been termed, for convenience, the "bottom 73" of cartridge 71 is, in reality, the forwardmost surface of the cartridge assembly 66 and faces anvil 65 (see FIG. 21). Near its end 75, the exterior surface of bottom 73 is provided with a forwardly extending spacer element 83 adjacent to perforation 81, as is shown in FIG. 25. Similarly, the outside surface of bottom 73, near cartridge end 76, is provided with a forwardly extending spacer element 84 extending partway about the outermost end of slot 82. The spacers 83 and 84 cooperate with anvil 65 (see FIG. 21) to determine the forwardmost position of cartridge assembly 66.

Referring now to FIG. 26, cartridge 71 is provided with a centrally located, longitudinally extending, upstanding interior wall, generally indicated at 85. The wall 85 is provided with a plurality of vertical slots 86 which divide the wall 85 into alternating narrow upstanding elements 87 and wide upstanding elements 88. The endmost wide elements 88a and 88b are slightly narrower than the remaining wide elements 88 and are notched at their outermost edges, as at 88c and 88d, as is shown in FIG. 28.

Referring again to FIG. 24, the interior wall 85 separates two rectilinear rows of slots 89 and 90. All of the slots 89 are identical, as are all of the slots 90. The slots 90 are mirror images of slots 89. It will be noted from FIG. 24 that the slots 90 are staggered with respect to the slots 89 and, therefore, are one less in number. The number of slots 89 and 90 does not constitute a limitation of the present invention.

A typical slot 89 is illustrated in FIG. 24a. The slot 89 in the cartridge bottom 73 is defined by a rectilinear outer wall 89a, a pair of rectilinear end wall portions 89b and 89c, a pair of arcuate end wall portions 89d and 89e, a pair of rectilinear end portions 89f and 89g similar to end wall portions 89b and 89c, a pair of rectilinear inner wall portions 89h and 89i, parallel to outer wall 89a, a pair of rectilinear inner wall portions 89j and 89k perpendicular to inner wall portions 89h and 89i, and a final inner wall portion 89l.

End wall portions 89b and 89c are so spaced from each other that they will just nicely engage the legs of a surgical staple with a frictional fit. The same is true of rectilinear end wall portions 89f and 89g. As a result, that portion of slot 89, defined by outer wall 89a and rectilinear end wall portions 89b and 89c, constitutes a storage pocket generally indicated at 91. A surgical staple is shown in storage pocket 91 in broken lines at 92. In a similar fashion, the rectilinear end wall portions 89f and 89g and the short rectilinear inner wall portions 89h and 89i constitute a forming pocket, the rectilinear end wall portions 89f and 89g being so spaced from each other as to just nicely engage the legs of a surgical staple with a frictional fit. The forming pocket portion of slot 89 is generally indicated at 93 and a surgical staple is shown therein in broken lines at 94. The storage pocket portion 91 of slot 89 is separated from forming pocket portion 93 by the shallow arcuate end wall portions 89d and 89e which are camming surfaces, as will be explained hereinafter. Inner wall portions 89j, 89k and 89m constitute or define an extended portion of slot 89 to accommodate a driver blade, as will be apparent hereinafter.

Figure 36:
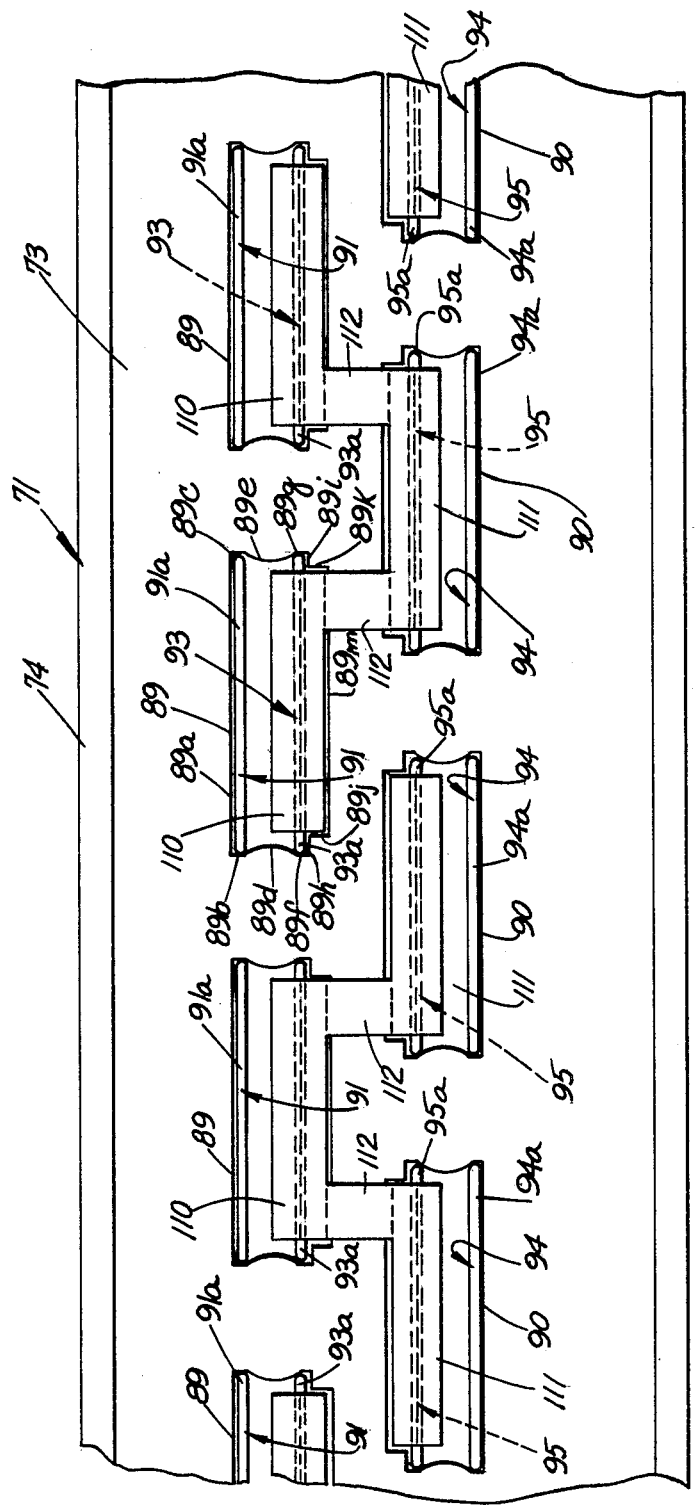
FIG. 36 is a fragmentary, simplified, semi-diagrammatic plan view of the cartridge, illustrating the position of the driver blades with respect to the cartridge forming and storage pockets.

In FIG. 36, the slots 89 have all of their wall portions 89a through 89m, together with their storage pockets 91 and its forming pockets 93 shown. Also, staples 91a are illustrated in storage pockets 91 and staples 93a are shown in forming pockets 93. It will be apparent from FIG. 36 that all slots 89 have an outer storage pocket provided with a surgical staple and an inner forming pocket also provided with a surgical staple. The same is true of all the slots 90, which are simple mirror images of the slots 89. Each slot 90 will have a storage pocket 94 equivalent to storage pocket 91 and a forming pocket 95 equivalent to forming pocket 93. In each of the slots 90, a surgical staple 94a is shown in storage pocket 94 and a surgical staple 95a is shown in forming pocket 95.

Figure 30:
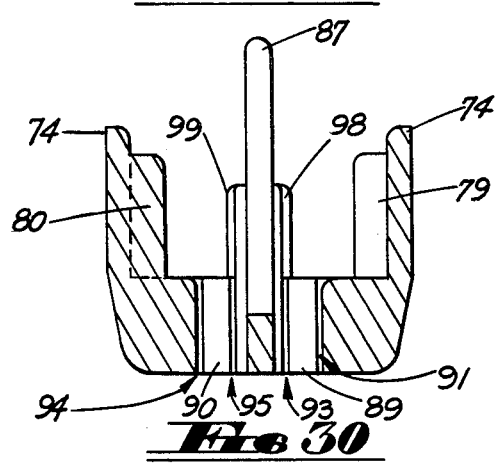
FIG. 30 is a fragmentary cross-sectional view taken along section line 30-30 of FIG. 29.
Figure 31:
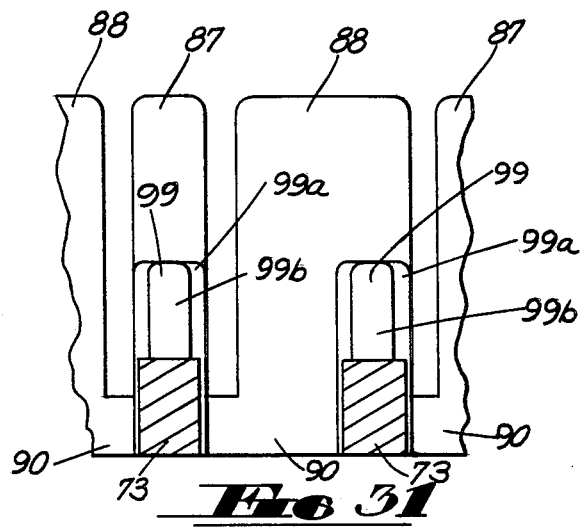
FIG. 31 is a fragmentary cross-sectional view taken along section 31—31 of FIG. 29.

Reference is now made to FIGS. 29, 30 and 31. As is most clearly seen in FIG. 29, vertical reinforcing walls 98 extend perpendicularly from each portion of bottom wall 73 which separates the adjacent slots 89. Similarly, reinforcing walls 99 extend perpendicularly from those portions of cartridge bottom 73 which separate adjacent slots 90. As is apparent from FIGS. 24 and 29, each interior wall portion 88 will have one reinforcing wall 98 and one reinforcing wall 99 constituting an integral part thereof. Depending upon its position, each interior wall portion 87 will have either one reinforcing wall 98 or one reinforcing wall 99 constituting an integral part thereof. All of the reinforcing walls 98 are identical, as are all of the reinforcing walls 99. The reinforcing walls 99 are simple mirror images of reinforcing walls 98. The tops of all of the reinforcing walls 98 and 99 are coplanar, as shown in FIG. 30.

Referring to FIG. 31, it will be apparent that each wall 99 comprises a wide portion 99a adjacent one of the inner wall portions 87 or 88, and portion 99a is of a width such that its side walls are coplanar with the end walls of each extension portion of adjacent slots 90. Thus, the portions 99a of reinforcing walls 99 serve as additional guides for the blades of driver 72, to be described hereinafter. Each wall 99 has an additional portion 99b adjacent the portion 99a and of lesser width. This ensures that the wall 99 will not interfere with the forming pockets 95 of slots 90. It will be remembered that reinforcing walls 98 are a mirror image of reinforcing walls 99 and are thus similarly configured.

Reference is now made to FIGS. 23 and 24. To complete the cartridge 71, it should be noted that the wall 74, at the cartridge end 75, has its interior surface so configured as to provide an end surface 100 substantially perpendicular to the long axis of interior wall 85. The end surface 100 terminates in a pair of parallel surfaces 101 and 102, both perpendicular to end surface 100 and both terminating in shoulders 103 and 104, respectively. The purpose of the inner surfaces 100-104 of wall 74 will be apparent hereinafter. At the other end 76 of cartridge 71, the interior surface of wall 74 is so configured as to provide a pair of shoulders or surfaces 105 and 106. The purpose of these surfaces will be apparent hereinafter.

The driver 107 will next be described, and reference is made to FIGS. 33, 34 and 35. The driver 107 is an integral, one-piece element comprising an elongated body 108, having at its ends hook-like elements 109 and 109a. Extending from body 108, there are a plurality of blades 110, arranged in a rectilinear row. In similar fashion, additional blades 111 extend from body 108. The blades 111 are also arranged in a rectilinear row. It will be noted that the blades 111 are staggered with respect to the blades 110 and, therefore, are one less in number. It will further be noted that the blades 110 are equal in number to the number of cartridge slots 89, while the blades 111 are equal in number to the number of cartridge slots 90.

As is most clearly shown in FIG. 33, driver blades 110 and 111 are arranged in alternating groups of three. Starting at the left end of FIG. 33, the first group comprises two blades 110 and one blade 111. The next group comprises two blades 111 and one blade 110, and so on. The blades of each group are joined together by webs 112 (see also FIG. 35). As is evident from FIG. 35, webs 112 are shorter than driver blades 110 and 111. Arranging the driver blades 110 and 111 in groups of three is a matter of convenience permitting cross bracing. Other groupings could be used. The webs 112 prevent spreading of driver blades 110 and 111 into the storage pockets 91 and 94.

FIG. 36 is a simplified representation of the cartridge 71 and driver 107. In FIG. 36, interior wall 85 of cartridge 71, together with cam elements 79 and 80 have been deleted for purposes of clarity. FIG. 36 illustrates two groups of driver blades 110 and 111, and their connecting webs 112. It will be noted that the driver blades 110 are so positioned as to be centered over the staples 93a in forming pockets 93 of slots 89. Similarly, driver blades 111 are centered over the staples 95a in forming pockets 95 of slots 90. It will be appreciated from FIG. 36 that when the driver is actuated, it will simultaneously drive the staples 93a and 95a from their respective forming pockets 93 and 95. Thus, two rows of staples, the staples of one row being staggered with respect to the other, will simultaneously be implanted in the tissue being sutured. It will be understood that the webs 112 extending between blades 110 and 111 will pass between the sections 87 and 88 of interior wall 85, through the slots 86 therebetween (see FIG. 28).

As is most clearly shown in FIG. 35, the free end of each driver blade 110 has a centrally located, longitudinally extending slot 110a. Similarly, the free end of each driver blade 111 has a centrally located, longitudinally extending slot 111a. When the free ends of driver blades 110 and 111 contact their respective surgical staples 93a and 95a, the staple crowns will be engaged in the longitudinal slots 110a and 111a. As is most clearly shown in FIGS. 33 and 34, the longitudinal slots 110a of driver blade 110 are interrupted at their longitudinal centers by transverse notches 110b. Similarly, the longitudinal slots 111a of driver blade 111 are interrupted at their longitudinal centers by transverse notches 111b. As is known in the art, the transverse notches 110b and 111b prevent staples from embedding in the driver blades 110 and 111 should they be over-formed.

Driver 107 is actuated by an elongated driver rod (not shown) located within the body 61 of instrument 60 (see FIG. 21). One end of the driver rod is operatively connected to trigger 63. The other end of the driver rod abuts the body 108 of driver 107 and is engaged by the hook-like portions 109 and 109a (FIG. 34), as described in the above noted co-pending application.

Figure 39:
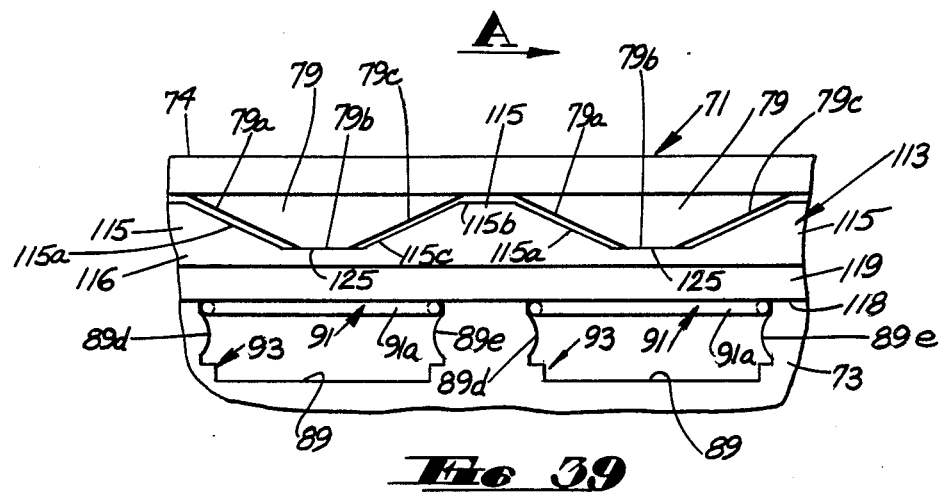
FIG. 39 is a fragmentary, simplified plan view of the cartridge and a slider, illustrating the slider in its initial, unactuated position.
Figures 37, 38:
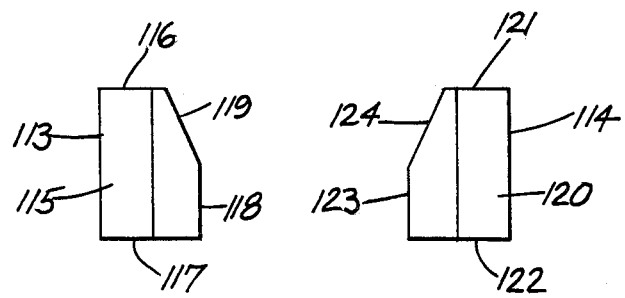
FIGS. 37 and 38 are end elevational views of the sliders of the cartridge assembly.
Figure 52:
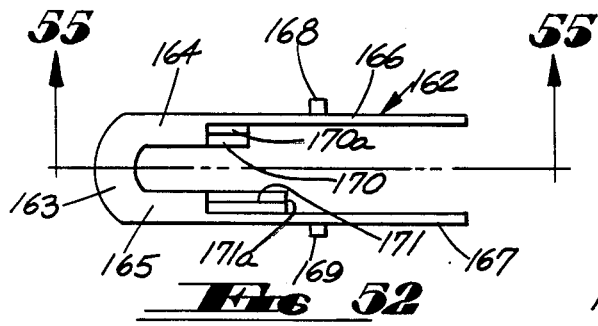
FIG. 52 is a plan view of the indexing button.
Figure 56:
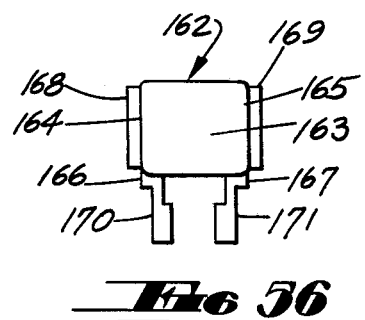
FIG. 56 is an end elevational view of the indexing button, as seen from the left of FIG. 53.
Figure 53:
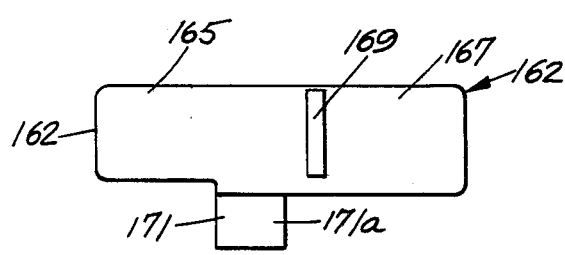
FIG. 53 is a side elevational view of the indexing button.
Figure 54:
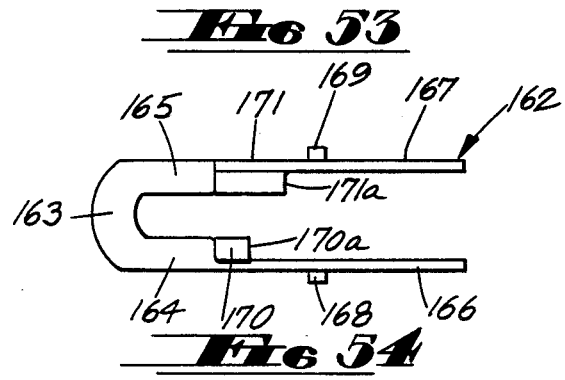
FIG. 54 is a bottom view of the indexing button.
Figure 57:
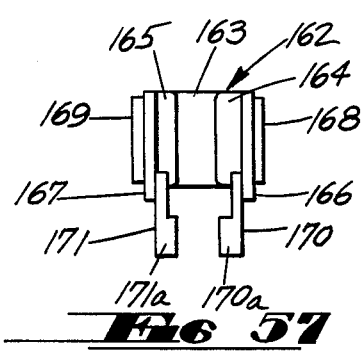
FIG. 57 is an end elevational view of the indexing button, as seen from the right of FIG. 53.
Figure 55:
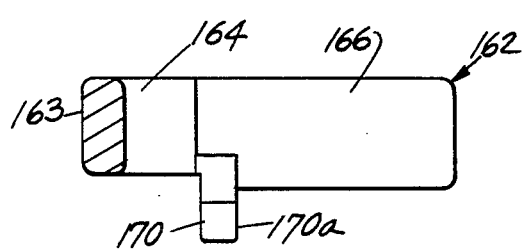
FIG. 55 is a cross-sectional view taken along section line 55—55 of FIG. 52.

FIG. 22 illustrates a pair of sliders 113 and 114. End views of sliders 113 and 114, as seen from the left in FIG. 22, are shown in FIGS. 37 and 38. It will be evident from FIGS. 22 and 37 that slider 113 comprises an elongated member, the outside surface of which is provided with a plurality of cam elements 115. The top surface 116 is planar, as is bottom surface 117. The inside surface 118 is also planar, oriented at 90° to bottom surface 117. Top surface 116 is joined to inside surface 118 by a downwardly sloping surface 119. Slider 114 is similarly configured, having a plurality of cam surfaces 120 on its outside surface, a planar top surface 121, a planar bottom surface 122 and a planar inside surface 123 oriented at 90° to bottom surface 122. As in the case of slider 113, the top surface 121 is joined to the inside surface 123 by a downwardly sloping surface 124. As is evident from FIGS. 22 and 45, sliders 113 and 114 are substantially mirror images of each other, with the exception that slider 114 has one less cam element than slider 113, making their end configurations slightly different. Nevertheless, sliders 113 and 114 are sufficiently similar that a detailed description of one will suffice for the other. Reference is made to FIG. 39 which is a simplified fragmentary view of cartridge 71 (its inner wall not shown) with slider 113 mounted therein.

In FIG. 39, slider 113 is shown in its initial, normal position. It will be noted that the cam members 115 of slider 113 are similar in configuration and nest with the cam members 79 of the inside surface of cartridge wall 74. Thus, each cam member has a surface 115a equivalent to surface 79a, a surface 115b substantially equivalent to that portion of the inside surface of wall 74 between cam members 79 and a surface 115c equivalent to surface 79c. It will further be noted that the surfaces just described are just slightly spaced from each other. Between cam elements 115, slider 113 has rectilinear surfaces 125 adapted to abut the surfaces 79b of cam elements 79. It will further be noted that the planar inner surface 118 of slider 113 lies adjacent the surgical staples 92 located in the storage pockets 91 of slots 89.

Figure 40:
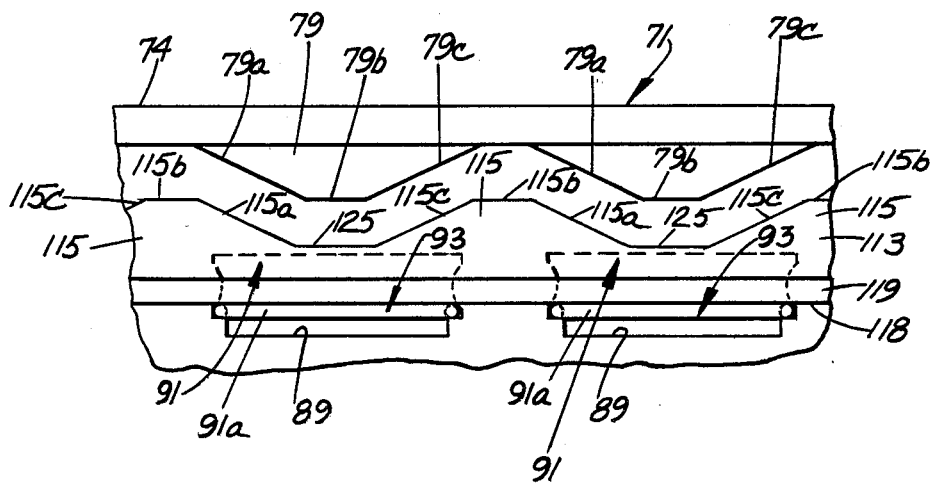
FIG. 40 is a fragmentary, simplified plan view of the cartridge and the slider of FIG. 39, illustrating the slider in its actuated position.

FIG. 40 illustrates what happens when slider 113 is indexed in the direction of arrow A of FIG. 39, such that each cam member 115 of slider 113 shifts to the other side of the next adjacent cam member 79 of cartridge wall 74. It will be apparent from FIG. 39 that when slider 113 is shifted in the direction of arrow A, cam surfaces 115a of the slider will contact and ride along corresponding cam surfaces 79a of the cartridge cams 79. Thus, slider 113 will not only move in the direction of arrow A in FIG. 39, it will also shift inwardly toward the center of cartridge 71, to the position illustrated in FIG. 40. This longitudinal and transverse movement of slider 113 will shift surgical staples 91a from the storage pockets 91 to the forming pockets 93 of slots 89. Thus, when the surgical staples 93a, originally located in forming pockets 93 of slots 89, have been implanted and clinched, the indexing of slider 113, as described with respect to FIGS. 39 and 40, will shift staples 91a to forming pockets 93 so that the instrument 60 can be actuated for a second time. It will be apparent from FIG. 39 that as the surgical staples 91a shift from storage pocket 91 to forming pocket 93, the legs of the staples 91a will have to bend slightly toward each other to enable them to shift past the arcuate end portions 89d and 89e of slots 89. When the forming pockets 93 are reached, the staples 91a will snap therein, being held by a frictional snap fit.

Slider 113 will remain in the position shown in FIG. 40. It will be apparent that in this position the slider 113 will interfere with driver blades 110 (see FIG. 36). However, as the driver blades 110 descend, they will first contact the beveled portion 119 of slider 113 which will cause the slider to shift toward cartridge side 74 and its cam elements 79, out of the way of driver blades 110.

It will be understood by one skilled in the art that slider 114 operates in exactly the same manner to shift staples 94a from storage pockets 94 of slots 90 to the forming pockets 95 of the slots 90.

Support plate 126 is shown in FIGS. 22 and 41–44. The support plate comprises an elongated member made up of side walls 127 and 128, together with end walls 129 and 130. The side walls 127 and 128 narrow considerably at 127a and 128a, adjacent the end 129. This narrowing of the side walls creates a pair of shoulders 131 and 132, the purpose of which will be described hereinafter. Side wall 127 has a pair of laterally extending lugs 133 and 134. Similarly, side wall 128 has a pair of laterally extending lugs 135 and 136. The purpose of lugs 133–136 will also be apparent hereinafter.

The inside surface of side wall 127 and its narrow portion 127a has a plurality of inwardly extending lugs 137 and 137a thereon. The lugs 137a, of which there are two, differ from lugs 137 only in that they extend above the top surface of side wall 127 and its narrow portion 127a. In a similar fashion, the inside surface of side wall 128 and its narrow portion 128a has a plurality of lugs 138, 138a and 138b. The lugs 138a (of which there are two) differ from lugs 138 in that they also extend above the surface of side wall 128 and its narrow portion 128a. The endmost lugs 138b (adjacent end walls 129 and 130) are somewhat elongated as shown in FIG. 41. To complete the structure, it will be noted that end wall 130 is of lesser height that adjacent side walls 127 and 128, creating a notch 139. The purpose of notch 139 will be described hereinafter.

FIG. 45 illustrates the cartridge 71 with sliders 113 and 114 mounted therein, together with support plate 126. Mounting of the support plate is achieved by virtue of the fact that all of the lugs 137 and 137a of side wall 127 and its narrow portion 127a rest upon reinforcing walls 98 of the interior wall 85. Similarly, all of the lugs 138, 138a and 138b of support plate side wall 128 and its narrow portion 128a rest upon support walls 99 of the cartridge interior wall 85. End walls 129 and 130 of support plate 126 rest in the notches 88c and 88d of cartridge interior wall endmost members 88a and 88b, respectively. In addition, the exterior lugs 133 and 134 of side wall 127 rest upon selected ones of the cartridge cam elements 79. In a similar fashion, the exterior lugs 135 and 136 of the support plate side wall 128 rest upon selected ones of cartridge cam elements 80. As will be made apparent hereinafter, the primary purpose of support plate 126 is to serve as an interior reinforcing member for the cartridge assembly 66. It will be understood that the blades 110 and 111 of driver 107 will extend through support plate 126.

The casing 140 is shown in FIGS. 22 and 46–51. The casing 140, in cooperation with cartridge 71, encloses the mechanism of the cartridge assembly 66. The casing comprises a hollow, bottomless housing having substantially planar side walls 141 and 142, a substantially planar end wall 143 and an arcuate end wall 144. Side walls 141 and 142 and end walls 143 and 144 have upwardly and inwardly beveled portions 141a, 142a, 143a and 144a, respectively, terminating in the planar casing top 145.

The casing top 145 has a longitudinal slot 146 and a pair of transverse slots 147 and 148. The transverse slot 147 extends through the beveled portion 141a and the adjacent part of side 141. Similarly, the slot 148 extends through beveled portion 142a and the adjacent part of side wall 142. The purpose of slots 146, 147 and 148 is to accommodate the driver rod and handle plates (not shown) of the instrument. These elements are fully described in the above noted co-pending application. The top 145 also has a perforation 149 which is coaxial with the perforation 81 of cartridge 71, and is also adapted to accommodate alignment and retaining pin 69.

The arcuate end wall 144 of casing 140 has a notch 150 adjacent the open end of casing 140. Side walls 141 and 142 have notches 151 and 152, respectively, adjacent the open end of casing 140 and near notch 150. Notches 150, 151 and 152 accommodate the indexing button of cartridge assembly 66, as will be described hereinafter.

Adjacent notch 151, the interior surface of side wall 141 has a cavity 153 formed therein. This is shown in FIGS. 50 and 51. That portion 141a of side wall 141 between notches 150 and 151 has the same thickness as the cavity portion 153. In a similar fashion, side wall 142 has a cavity 154 formed on its inside surface adjacent notch 152. That portion 142a of side wall 142 between notches 150 and 152 is of the same thickness of the cavity portion 154. Cavity portions 153 and 154 serve to accommodate the indexing button of the cartridge assembly 66, as will be apparent hereinafter.

To complete the structure of casing 140, side wall 141 has a pair of shallow notches 155 and 156 adjacent the open end of casing 140. Similarly, side wall 142 has, formed on its inside surface, shallow notches 157 and 158 near the open end of casing 140. When the casing 140 is mounted on cartridge 71, the interior notches 155 and 156 of side wall 141 will receive portions of the lateral lugs 133 and 134, respectively, of support plate 126. Similarly, the interior notches 157 and 158 of side wall 142 will receive portions of the lateral lugs 135 and 136 of support plate 126. The free edges of side walls 141 and 142 will abut the walls 74 of cartridge 71. That edge of planar end wall 143 of casing 140 adjacent the open end of the casing will be received in the notch 130 at the end wall 139 of support plate 126. The abutting surfaces of the cartridge 71 and casing 140 can be joined together by any appropriate means, such as adhesive means, sonic welding or the like. These abutting edges may be given a ship-lap configuration, if desired.

Turning briefly to FIG. 63, casing 140 is shown mounted on cartridge 71. It will be noted that those edges of casing sides 141 and 142 adjacent the open end of the casing are in abutment with the surrounding wall 74 of cartridge 71. As indicated above, the engagement of these edges could be a ship-lap engagement, and they are joined together by any suitable means, such as adhesive, sonic welding or the like. Since the cartridge assembly is intended for use in a surgical environment, sonic welding is frequently preferred. FIG. 63 also illustrates sliders 113 and 114, driver 107 and support plate 126.

The handle plates of the instrument 160, fully described in the above mentioned co-pending application, are fragmentarily shown in FIG. 63 at 160 and 161. Handle plates 160 and 161 constitute part of the mechanism by which a compressive force is applied to the tissue located between the cartridge assembly 66 and anvil 65, during achievement of the proper gap within the working gap of the instrument, prior to the suturing or stapling operation. One of the functions of support plate 126 is to transmit the force from handle plates 160 and 161 to the cartridge 71.

Referring to FIGS. 41–44, it will be remembered that the lugs 137a and 138a extend above the side walls of support plate 126. One pair of lugs 137a–138a is shown in broken lines in FIG. 63. The function of these lugs is to maintain proper spacing between those portions of handle plates 160 and 161 within the cartridge assembly 66 to assure clearance between them and driver 107. The other pair of support plate upstanding lugs 137a and 138a, not shown in FIG. 63, serve the same purpose.

FIG. 63 also illustrates the lateral lugs 155 and 157 of support plate 126, engaged in the notches 155 and 157, respectively, of the casing side walls 141 and 142. It will be understood that support plate lugs 134 and 136 will similarly be engaged in casing notches 156 and 158, respectively. As a result of this, support plate 126 contacts both the casing walls 141 and 142 and the surrounding wall 74 of cartridge 71. It will further be remembered that each of the support plate interior lugs 137 and 137a abut and are supported by reinforcing walls 98 while support plate lugs 138, 138a and 138b abut and are supported by reinforcing walls 99 (see FIG. 45). Furthermore, each of the larger segments 88 has a reinforcing wall 98 and a reinforcing wall 99 constituting an integral part thereof. Therefore, there is complete bracing transversely across the cartridge assembly 66 against any transverse compressive forces. It will be noted from FIG. 63 that the support plate 126 is located above sliders 113 and 114 and, therefore, cannot interfere with their operation.

Reference is now made to FIGS. 22 and 52–57, wherein indexing button 162 is illustrated. Indexing button 162 comprises a U-shaped member having an arcuate base portion 163 terminating in parallel leg portions 164 and 165. Leg portion 164, itself, terminates in a thin leg portion 166, while leg portion 165 similarly terminates in a thin leg portion 167. Leg portions 166 and 167 are also parallel and are coextensive.

On its exterior surface, the leg portion 166 carries an integral indicator 168 extending transversely thereof. The exterior surface of leg portion 167 carries an identical indicator 169 extending transversely thereof and aligned with indicator 168.

To complete the structure of indexing button 162, leg portion 166 has an integral lug 170 extending downwardly from its inside surface. Leg portion 167 also has a lug 171 extending downwardly from its inside surface. As is most clearly seen in FIGS. 55 and 56, the free ends of lugs 170 and 171 are enlarged so as to present abutment surfaces 170a and 171a facing away from indexing button base portion 163. Abutment surfaces 170a and 171a are intended to contact the ends of sliders 113 and 114, respectively, so that the indexing button can be used to shift or index the sliders simultaneously. It will be noted from FIGS. 52-55 that the lug 70 is of a lesser transverse length than the lug 171. This takes into account the difference in lengths of the sliders 113 and 114.

FIGS. 58, 59 and 63 illustrate indexing button 162 mounted in cartridge assembly 66. In all of these Figures, the indexing button is shown in its normal, unactuated position. It will be noted that the base portion 163 and the majority of leg portions 164 and 165 extend beyond the confines of cartridge 71 and casing 140 through the notch 150 in the rounded end 144 of casing 140. Thin leg portions 167 and 166 of indexing button 162 are supported by cartridge cam elements 80 and 79, respectively. Downwardly depending lug 170 lies along the inside surface portion 101 of cartridge wall 74 (see also FIG. 24). Similarly, the downwardly depending lug 171 of indexing button 162 lies along the inside surface portion 102 of cartridge wall 74. The indexing button lugs 170 and 171 also abut the inside surface portion 100 of cartridge wall 74. Since indexing button 162 is substantially U-shaped, it will be understood that it will not interfere with cartridge perforation 81 or alignment and retaining pin 69 extending therethrough. The abutment surfaces 170a and 171a are located adjacent the ends of sliders 113 and 114, respectively.

The large notch 151 of casing side 141 serves as a window through which indexing button indicator 168 can be easily viewed. Similarly, the large notch 162 in the casing side 142 serves as a window through which indexing button indicator 169 can be viewed. Either the casing 140 or the cartridge 71 can be provided with indicia cooperating with indexing button indicators 168 and 169. For purposes of an exemplary showing, the cartridge portion of cartridge assembly 66 is shown (in FIG. 21) provided with the numerals "1" and "2". As shown in FIG. 21, when the indexing button 162 is in its normal, unactuated position, its indicator 169 will align with the numeral "1" on the cartridge. The same sort of indicia may be provided on the other side of the cartridge to cooperate with indicator 168.

It will be apparent from FIGS. 58, 59 and 63 that if indexing button 162 were shifted in the direction of arrow B in FIG. 59, the abutment surfaces 170a and 171a would engage the ends of sliders 113 and 114, causing them to index as described above. As will be apparent from FIG. 45, when sliders 113 and 114 are indexed, the ends opposite those ends contacted by abutment surfaces 170a and 171a of indexing button 162 will abut the inside surface portions 105 and 106 of cartridge wall 74 to prevent over-indexing. Furthermore, support plate shoulders 131 and 132 act as stop surfaces for indexing button 162. Returning to FIG. 21, once indexed, the indicator 169 will align with the numeral "2" on cartridge 71, the same being true of indexing button indicator 168. This is a clear visual indication to the surgeon that the second load of staples has been shifted from the storage pockets to the forming pockets of cartridge 71 and are ready for implanting and forming by a second actuation of instrument 60.

The cartridge assembly 66 is completed by safety 172 illustrated in FIGS. 22 and 60-62. The purpose of safety 172 is to prevent indexing of indexing button 102 and sliders 113 and 114 when staples are still present in forming pockets 93 and 95. In this way, proper sequencing of the cartridge assembly 66 is assured and jamming is precluded.

The safety 172 comprises an elongated shank 173 of uniform width and thickness terminating at its upper end, as viewed in FIGS. 61 and 62 in an enlarged portion 174. At its lower end, the shank 173 terminates in an enlarged portion 175, somewhat larger than the enlarged end 174. The enlarged end 175 provides an abutment surface 176 intended to cooperate with the abutment surface 171a of lug 171 on indexing button 162.

Safety 172 is shown in its normal position within cartridge assembly 66 in FIG. 63. It will be noted that the shank portion 173 extends through the support plate 126 at the juncture of end wall 129 and lug 138b of narrow side wall portion 128a (see also FIG. 41). The enlarged end 175 is located just beneath support plate 126 while the enlarged end 174 is located beneath a shoulder 107a of driver 107 (see also FIGS. 34 and 35). When safety 172 occupies the position shown in FIG. 63, its abutment surface 176 faces abutment surface 171a of indexing button 162 and precludes movement thereof.

The bottom 73 of cartridge 71 is provided with a perforation 177 so sized as to just nicely receive the enlarged end 175 of safety 172. It will be apparent from FIG. 63 that when the instrument is actuated for a first time, causing driver 107 to shift downwardly and to implant and form the staples 93a and 95a in forming pockets 93 and 95, the shoulder 107a of driver 107 will contact the uppermost surface of the enlarged safety end 174, causing the safety 172 to shift downwardly. This will cause the enlarged end 175 of the safety 172 to enter the perforation 177 in cartridge 71, clearing the way for indexing of indexing button 162 and sliders 113 and 114, as soon as driver 107 is returned to its normal retracted position. The downwardmost position of safety 172 is determined by the abutment of its upper enlarged end 174 against the top surface of support plate 126.

The cartridge assembly 66 of the present invention, having been described in detail, its operation may now be set forth. In the particular embodiment shown, the cartridge assembly 66 comprises a permanent part of instrument 60. When the surgeon receives instrument 60, it will be in the condition shown in FIG. 21 with the cartridge assembly 66 spaced from anvil 65 and the alignment and retaining pin 69 in its retracted position. The surgeon locates the tissue to be sutured between the cartridge assembly 66 and the anvil 65, and then shifts the alignment and retaining pin 69 to its operating position by handle 70. In this position, the alignment and retaining pins 69 extends through the cartridge assembly 66 and into a suitable perforation in fixed jaw 64, trapping the tissue to be sutured between anvil 65 and cartridge assembly 66.

This having been accomplished, the surgeon next sets the gap or distance between the cartridge assembly 66 and the anvil 65, within the working gap of the instrument, in accordance with the procedures set forth in the above noted co-pending application. Thereafter, trigger 63 is actuated, causing driver 107 to shift the staples 93a and 95a in forming pockets 93 and 95 through the tissue and against the anvil 65, thus implanting and clinching these staples to form a double, staggered row of staple sutures. This having been done, the cartridge assembly 66 is shifted to its retracted position, as is alignment and retaining pin 69, and the instrument is removed from the sutured tissue.

As indicated above, the first actuation of driver 107 will simultaneously shift cartridge assembly safety 172 from its disabling to its enabling position. The surgeon is now free to push indexing button 162 with respect to assembly 166, thus indexing sliders 113 and 114 and shifting surgical staples 91a and 94a from holding pockets 91 and 94 to forming pockets 93 and 95. Indexing button indicators 168 and 169 will show that this has been done and that the instrument is ready for a second use. At this point, the stapling procedure just described can be repeated. After the second actuation of the instrument 60, the instrument, together with the cartridge assembly 66, is disposed of.

While the cartridge assembly 66 may be appropriately constructed for refilling and reuse, it lends itself well to manufacture as a single-use, disposable unit. The various parts illustrated in FIG. 22 can be molded of plastic material suitable for a surgical environment and capable of being sterilized by autoclave, ethylene oxide, irradiation, or other standard methods.

In the embodiments thus far described, when the surgical staples in the forming pockets have been formed and implanted, at least a second set of staples is introduced into the forming pockets directly from storage pockets, or from staging pockets located between the forming pockets and the storage pockets. It is within the scope of the invention to provide an embodiment of the cartridge assembly wherein, after the first set of staples in the forming pockets have been implanted and formed, the forming pockets are moved from the line of action between the driver and the anvil, and the storage pockets, containing a second set of surgical staples, are shifted into the line of action between the driver and the anvil, thus becoming forming pockets. This arrangement is illustrated in simplified, diagrammatic form in FIGS. 65–68.

Figure 65:
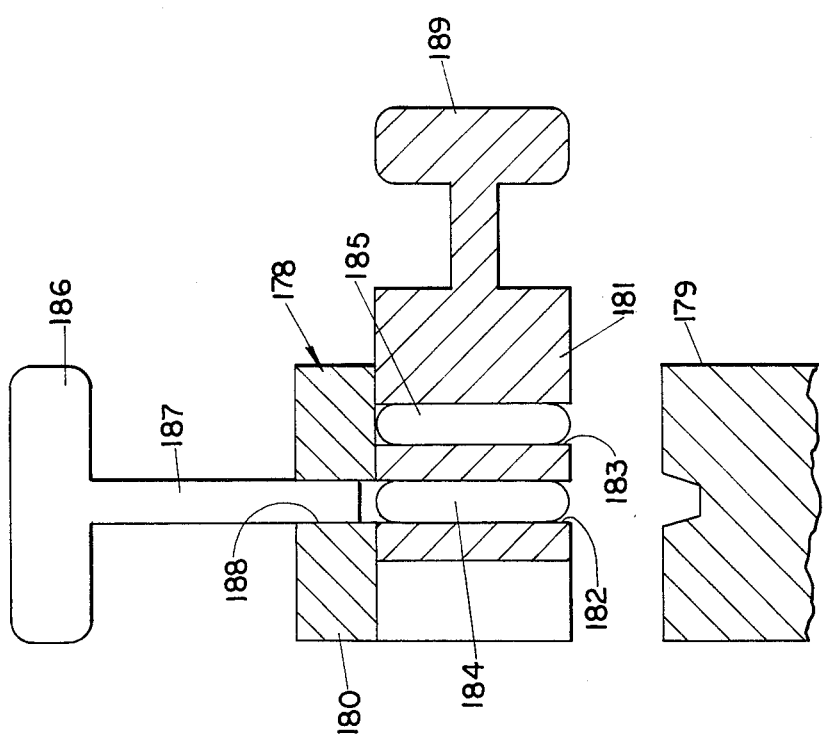

Reference is first made to FIG. 65, wherein a cartridge assembly is generally indicated at 178. The anvil of a linear surgical stapling instrument is diagrammatically indicated at 179. The magazine assembly 178 comprises a body 180 and a plunger-like element 181 shiftable transversely with respect to body 180. The plunger-like element 181 contains a row of forming pockets, the endmost one of which is shown at 182. The plunger-like element 181 contains a row of storage pockets, the endmost one of which is shown at 183. Each of the forming pockets and each of the storage pockets is provided with a surgical staple. A surgical staple 184 is shown in endmost forming pocket 182 and a surgical staple 185 is shown in endmost storage pocket 183. The number of storage pockets is equal to the number of forming pockets.

The cartridge assembly 178 has a driver 186. The driver 186 is provided with a plurality of blades equal in number to the number of forming pockets. The endmost driver blade is shown at 187. The body 180 has a slot for each driver blade. The endmost slot for driver blade 187 is shown at 188. To complete the diagrammatic representation of FIG. 65, the plunger-like element 181 is provided with a handle-like element 189, representing an indexing mechanism.

FIG. 65 illustrates the cartridge assembly 178 in its initial, fully loaded condition. It will be understood that the cartridge assembly 178 will be mounted on a linear surgical stapling instrument (not shown). The operation of the cartridge assembly 178 will be described in terms of forming pocket 182, storage pocket 183 and staples 184 and 185. It will be understood that precisely the same things will occur in all of the forming pockets and storage pockets.

Figure 66:
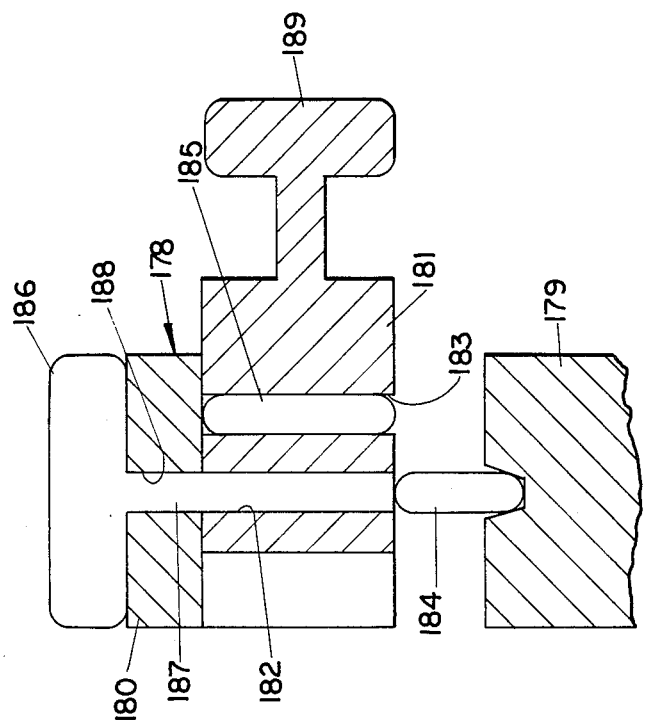
FIGS. 65—68 are diagrammatic representations, partly in cross section, illustrating an embodiment of the invention and its sequential operation wherein the loaded storage pockets move linearly as an array to replace the emptied forming pockets.

When the linear surgical stapling instrument (not shown) is actuated for a first time, the driver 186 will shift downwardly as viewed in FIG. 65 to the position shown in FIG. 66. This will drive the staple 184 from forming pocket 182, through tissue (not shown) located between the cartridge assembly 178 and the anvil 179, and will cause the staple 184 to be formed by anvil 179.

Figure 67:
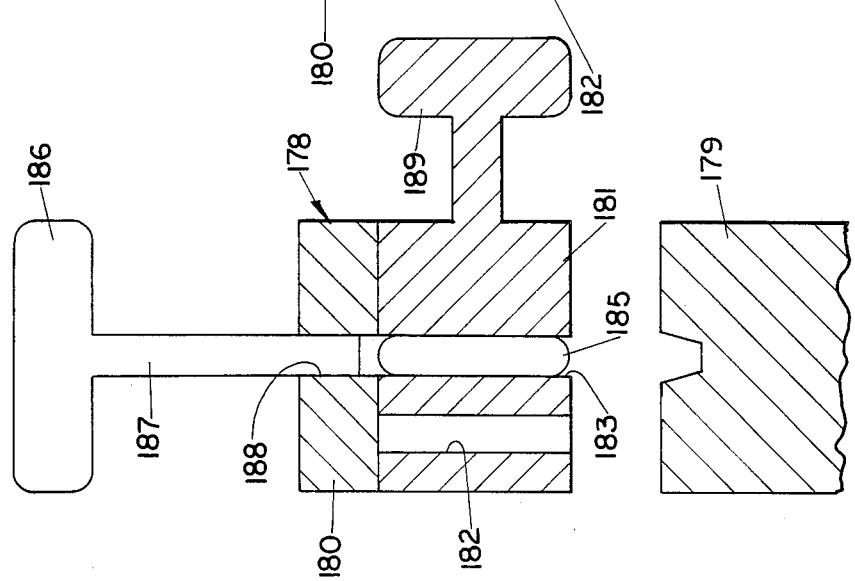

After the first actuation of the linear surgical stapling instrument, the driver 186 is withdrawn to its normal retracted position, as shown in FIG. 67. At this point, the indexing mechanism 189 is used to shove the plunger-like element 181 to the left as viewed in FIGS. 65–68, to the position shown in FIG. 67. This movement of the plunger-like member 181 shifts the forming pocket 182 from the line of action between driver 186 and anvil 179. This, of course, is true of all of the forming pockets. Simultaneously, storage pocket 183 (and all of the other storage pockets) are shifted into the line of action between the driver 186 and anvil 179. This is illustrated in FIG. 67. It will be seen from FIG. 67 that with the plunger-like element 181 in the position shown, the storage pocket 183 (and the other storage pockets), in essence, become or are converted to forming pockets.

Figure 68:
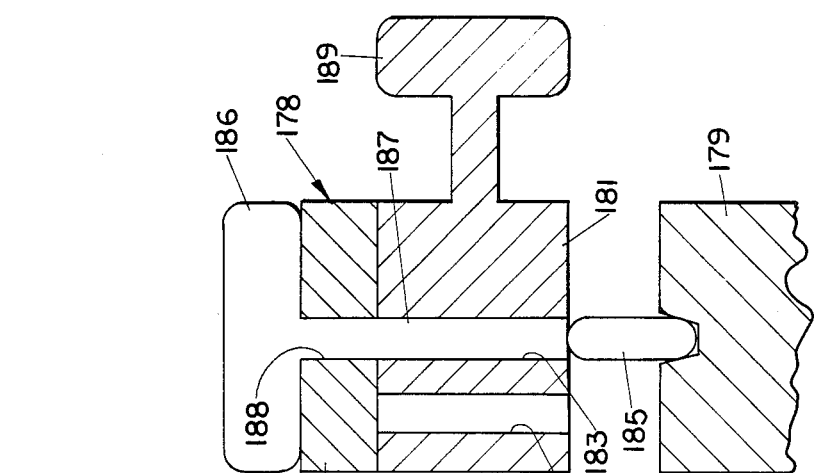

At this point, the linear surgical stapling instrument can be actuated for a second time. This will cause staple 185 of pocket 183 to be driven from pocket 183 (and all of the other staples to be driven from the equivalent pockets), through tissue (not shown) between the cartridge assembly 178 and the anvil 179, and to be clinched by the anvil 179. This is shown in FIG. 68.

The cartridge assembly 178 of FIGS. 65–68 constitutes a simple example of a two-load cartridge assembly. It will be understood that the plunger-like element 181 could be provided with additional rows of storage pockets, each row (in its turn) being shiftable into the line of action between driver 186 and anvil 179.

In the embodiment just described, the forming pocket 182 (and the other forming pockets therebehind) and the storage pocket 183 (and the other storage pockets therebehind) are shifted in a rectilinear path of travel. It will be understood that other paths of travel could be used. To illustrate this, reference is made to the embodiment of FIG. 69.

Figure 69:
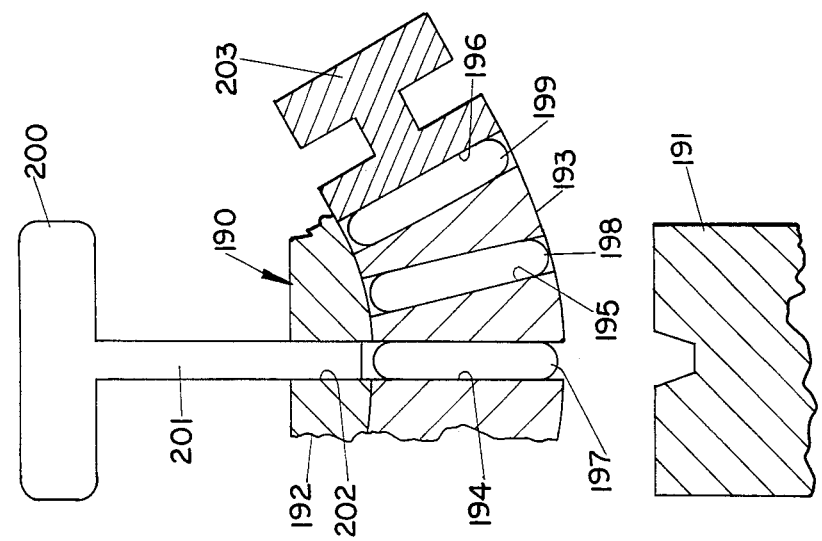
FIG. 69 is a diagrammatic representation, partly in cross section, of an embodiment similar to that of FIGS. 65-68, with the forming and storage pockets moving in an arcuate path.

In FIG. 69, a cartridge assembly is generally indicated at 190, together with an anvil 191. The cartridge assembly 190 comprises a body 192 and a member 193 rotatable with respect thereto. The member 193 is provided with a row of forming pockets, the endmost one of which is shown at 194. The member 193 is provided with one or more rows of storage pockets. For purposes of an exemplary showing, the member 193 is shown as having two rows of storage pockets, the endmost storage pocket of each row being shown at 195 and 196, respectively. Each forming pocket and each storage pocket is provided with a surgical staple. To this end, forming pocket 194 is shown provided with a surgical staple 197. Storage pockets 195 and 196 are shown provided with surgical staples 198 and 199, respectively. Again, it will be understood that the number of storage pockets in each row thereof will be equal and will be equal to the number of forming pockets.

A driver is illustrated at 200. The driver will have a blade for each forming pocket. The endmost blade of driver 200 is shown at 201. The body 192 of cartridge assembly 190 will have slots formed therein equal in number to the driver blades and adapted to slidably receive the driver blades. The endmost slot of body 192 is indicated at 202. Finally, to complete the cartridge assembly 190 of FIG. 69, the member 193 is shown as having a handle-like element 203, diagrammatically representing an indexing means.

Again, it will be understood that the cartridge assembly 190 will be affixed to an appropriate linear surgical stapling instrument (not shown). In FIG. 69, the cartridge assembly is illustrated in its initial, fully loaded condition. Upon a first actuation of the linear surgical stapling instrument, the driver 200 will shift the staple 197 of forming pocket 194 out of forming pocket 194, through tissue (not shown) located between the cartridge assembly 190 and the anvil 191, and will cause the clinching of staple 197 by anvil 191. It will be understood that surgical staples located in the other forming pockets (not shown) will be similarly implanted and formed.

Thereafter, the driver 200 is returned to its normal position illustrated in FIG. 69 and the indexing element 203 may be used to rotate member 193 so that the row of forming pockets represented by forming pocket 194 will be shifted out of the line of action between driver 200 and anvil 191, and the row of storage pockets, represented by storage pocket 195, will be shifted into the line of action between driver 200 and anvil 191, becoming the equivalent of forming pockets. The linear surgical stapling instrument (not shown) can now be actuated for a second time, and the driver 200 will cause the row of staples represented by staple 198 to be shifted from storage pockets represented by storage pocket 195 through tissue (not shown) located between cartridge assembly 190 and anvil 191, and to be clinched or formed by the anvil 191.

At this stage, the driver 200 can again be returned to its normal position shown in FIG. 69 and the indexing element 203 can be used to cause the member 193 to rotate again, shifting the row of storage pockets represented by storage pocket 195 out of the line of action between driver 200 and anvil 191 and locating the storage pockets represented by storage pocket 196 within this line of action. The storage pockets represented by storage pocket 196 thus become the equivalent of forming pockets. At this point, the surgical stapling instrument can again be actuated. This will result in the driver 200 shifting the staples represented by staple 199 from the storage pockets represented by storage pocket 196, through tissue (not shown) located between the cartridge assembly 190 and anvil 191, causing these staples to be clinched or formed by the anvil 191.

In the embodiment of FIG. 69, as is true of the embodiment of FIGS. 65-68, the number of rows of storage pockets does not constitute a limitation. In the embodiment of FIGS. 65-68 and the embodiment of FIG. 69, safety interlocks and load counting means have been omitted for purposes of clarity. It will be understood that such elements could, and preferably would, be provided with each embodiment. Both embodiments could constitute disposable cartridge assemblies, reusable and refillable cartridge assemblies, or could be incorporated into a completely disposable instrument. As was described with respect to the embodiments of FIGS. 5-20, efficient design of the cartridge assemblies would allow for single inputs from the surgeon via the linear surgical stapling instrument to result in several motions within the cartridge. Again, some form of stored energy source could be associated with the cartridge assemblies to partially or fully operate them. In all of the embodiments of FIGS. 1-20 and FIGS. 65-69, the driver, or the anvil, or both, could constitute a part of the multiple load cartridge assembly, itself.

In the above description, terms such as "top", "bottom", "upper", and "lower", are used in conjunction with the drawings for purposes of clarity. One skilled in the art will understand that during use, the instrument 60 may assume any desired or required orientation.

Modifications may be made in the invention without departing from the spirit thereof.

What is claimed is:

1. A surgical stapling instrument for implanting at least one linear row of staples in tissue, comprising:
   anvil means;
   means for driving staples aginst said anvil means;
   a first linear array of staples located in a first position within said instrument aligned between said driving means and said anvil means;
   at least a second linear array of staples located in a second position within said instrument out of alignment with said driving means and said anvil means;
   means for actuating said driving means to move said first linear array of staples from said first position and clinch said first array of staples against said anvil means; and
   means for transferring said second array of staples from said second position to said first position after a first operation of said actuating means to enable a second operation of said actuating means.

2. The instrument of claim 1, further comprising first storage means for storing a linear array of staples at said first position and second storage means for storing a linear array of staples at said second position.

3. The instrument of claim 2, wherein said transfer means includes means for indexing said first storage means out of said first position while indexing said second storage means from said second position to said first position.

4. The instrument of claim 3, further including third storage means for storing a third linear array of staples at a third position, and fourth storage means for storing a fourth linear array of staples at a fourth position.

5. The instrument of claim 4, wherein said transfer means further includes means to ultimately index each of said storage means to said first position.

6. The instrument of claim 5, further including means for indicating which of said storage means is in said first position.

7. The instrument of claim 2, wherein said first storage means comprises a plurality of forming pockets and said second storage means comprises a plurality of storage pockets.

8. The instrument of claim 7, wherein each of said storage pockets corresponds to a forming pocket and is located adjacent thereto.

9. The instrument of claim 8, wherein said first array of staples includes one staple in each of said forming pockets and said second array of staples includes at least one staple in each of said storage pockets.

10. The instrument of claim 9, wherein said transfer means includes means for indexing a staple from each of said storage pockets to its corresponding forming pocket after each operation of said actuating means.

11. The instruement of claim 7, wherein said forming pockets are arranged in at least two rows which are longitudinally staggered.

12. The instrument of claim 1, wherein said transfer means comprises means for individually shifting each of the staples contained in said second array from said second position to said first position.

13. The instrument of claim 1, further comprising safety means for preventing a second operation of said actuating means before operation of said transfer means.

14. The instrument of claim 1, including means for indicating which of said arrays of staples is positioned in said first position.

15. A surgical stapling instrument for simultaneously implanting a plurality of staples arranged in at least one linear row in tissue, comprising:
   anvil means;
   means for driving staples against said anvil means;
   first cartridge means for holding a plurality of staples arranged in at least one linear array in a first position aligned between said driving means and said anvil menas;
   second cartridge means for holding a plurality of staples arranged in at least one linear array in a second position out of alignment with said driving means and said anvil means;
   means for actuating said driving means to move said staples from said first cartridge means and clinch said staples against said anvil means; and
   means for indexing said second cartridge means from said second position to said first position, after a first operation of said actuating means, to enable a second operation of said actuating means.

16. The instrument of claim 15, wherein said first and second cartridge means are contained within a unitary cartridge assembly.

17. The instrument of claim 16, wherein said cartridge assembly is removably mounted on said instrument.

18. The instrument of claim 17, wherein said cartridge assembly is disposable.

19. The instrument of claim 17, wherein said cartridge assembly may be removed from said instrument, refilled with staples and replaced in said instrument, allowing said cartridge assembly to be reused.

20. The instrument of claim 16, wherein said instrument comprises a disposable instrument.

21. The instrument of claim 15, further including means for indicating which of said cartridge means is located at said first position.

22. A surgical stapling instrument for forming and implanting at least one linear row of surgical staples in tissue, comprising:
   a frame terminating at its forward end in a fixed jaw;
   an anvil mounted on said fixed jaw;
   a cartridge assembly, slidably supported by said frame and shiftable longitudinally thereon, containing at least one linear row of forming pockets, each of which contains a staple, and a plurality of staple-carrying staging pockets, each of which is coupled to a corresponding forming pocket;
   means slidably mounted within said cartridge assembly for driving said staples from said forming pockets against said anvil;
   means for actuating said staple driving means between a retracted position and a staple driving position; and
   means for transferring a staple from each of said staging pockets to its corresponding forming pocket after a first operation of said actuating means, to enable another operation of said actuating means.

23. The instrument of claim 22, wherein said cartridge means further includes a plurality of storage pockets, coupled to each of said staging pockets, for storing at least one staple in each pocket thereof.

24. The instrument of claim 23, further including second transfer means for moving a staple from each of said storage pockets to its corresponding staging pocket upon operation of said first transfer means.

25. The instrument of claim 24, wherein said first and second transfer means operate simultaneously.

26. The instrument of claim 22, wherein said anvil, said staple driving means and said cartridge assembly comprise a disposable unit which is removably mounted on said frame.

27. The instrument of claim 22, wherein said cartridge assembly is removably mounted on said frame, and said pockets thereof are capable of being refilled with staples.

28. The instrument of claim 22, wherein said forming pockets are arranged in at least two linear rows which are longitudinally staggered.

29. The instrument of claim 22, further comprising safety neans for preventing operation of said indexing means when staples are present in said forming pockets.

30. The instrument of claim 22, wherein said anvil and said cartridge assembly comprise a disposable unit which is removably mounted on said frame.

31. The instrument of claim 22, further comprising means for indicating that said transfer means has operated.

32. A linear surgical stapling instrument for simultaneously forming and implanting at least one linear row of surgical staples in tissue, comprising:
   anvil means;
   means for driving staples against said anvil means;
   cartridge means for holding a plurality of staples, said cartridge means containing a first set of pockets arranged in at least one linear row aligned between said driving means and said anvil means and a second set of pockets coupled to each of said first pockets, wherein each of said pockets contains a staple;
   means for actuating said driving means to move said staples from said first set of pockets of said cartridge means and clinch said staples against said anvil means; and
   means for transferring said staples from said second set of pockets to said first set of pockets, after a first operation of said actuating means, to enable a second operation of said actuating means.

33. The instrument of claim 32, wherein said first set of pockets is arranged in at least two staggered linear rows.

34. The instrument of claim 32, wherein said cartridge means comprises a disposable unit which is removably mounted on said instrument.

35. A multiple load cartridge for use in a surgical stapling instrument having anvil means for simultaneously implanting in tissue a plurality of surgical staples arranged in at least one linear row, comprising;
   means for driving staples against said anvil means;
   cartridge means for holding a plurality of staples, said cartridge means containing a first set of pockets arranged in at least one linear row and aligned between said driving means and said anvil means and a second set of pockets corresponding to each of said first pockets and arranged in at least one linear row, wherein each of said pockets contains a staple;

means for actuating said driving means to move said staples from said frist set of pockets and clinch said staples aganist said anvil means to implant said staples in tissue;

first means for indexing said first set of pockets out of alignment with said driving means and said anvil means; and second means for indexing said second set of pockets into alignment between said driving means and said anvil means, after operation of said actuating means and said first indexing means, whereby a second operation of said actuating means is enabled.

36. The assembly of claim 35, wherein said driving means and said cartridge means are contained in a unitary cartridge assembly which is removably mounted on said surgical stapling instrument.

37. The assembly of claim 36, wherein said unitary cartridge assembly is disposable.

38. The assembly of claim 36, wherein said unitary cartridge assembly comprises a reusable unit which may be refilled with staples.

39. A multiple-load cartridge assembly for use with a linear surgical stapling instrument of the type having an anvil and a staple driver actuator which, when actuated, simultaneously implants at least one linear row of surgical staples in the tissue of a patient and clinches said surgical staples of said at least one row against said anvil, said cartridge assembly comprising a cartridge having at least one linear row of staple-containing forming pockets, a driver mounted within said cartridge assembly and shiftable therein by said driver actuator between a retracted position and an extended position, said driver having a plurality of blades equal in number to the number of said forming pockets and configured to enter said forming pockets and drive said staples therein through said tissue and against said anvil when shifted from said retracted position to said extended position by operation of said staple driver actuator, said cartridge assembly having a plurality of storage pockets equal in number to said forming pockets and each containing at least one staple and an indexing means to shift said at least one staple in each storage pocket to the adjacent one of said forming pockets to reload said forming pockets after the first operation of said staple driver actuator.

40. The cartridge assembly claimed in claim 39, including a safety means to disable said indexing means until said forming pockets are emptied by said driver.

41. The cartridge assembly claimed in claim 39, having at least two staggered linear rows of staple-containing forming pockets and a staple-containing storage pocket for each of said forming pockets.

42. The structure claimed in claim 41, including an equal number of surgical staples, greater than one, in each of said storage pockets, said indexing means being capable of shifting a staple from each of said storage pockets to its respective forming pocket after each operation of said driver actuator to introduce a staple load into said forming pockets.

43. The cartridge assembly claimed in claim 39, including visual indicator means showing the number of the load of surgical staples in said forming pockets.

44. The cartridge assembly claimed in claim 39, including an equal number of surgical staples, greater than one, in each of said storage pockets, and including a staging pocket between each storage pocket and its respective forming pocket, said indexing means comprising a first indexer to shift a staple from each storage pockets to its respective staging pocket when empty and a second indexer to shift a staple from each staging pocket to its respective forming pocket to reload said forming pocket after each operation of said driver actuator.

45. The structure claimed in claim 39, including an equal number of surgical staples, greater than one, in each of said storage pockets, said indexing means being capable of shifting a staple from each of said storage pockets to its respective forming pocket after each operation of said driver actuator to introduce a staple load into said forming pockets.

46. A multiple load cartridge assembly for use with a linear surgical stapling instrument of the type having an anvil and a staple driver actuator which, when actuated, simultaneously implants at least one linear row of surgical staples in the tissue of a patient and clinches said surgical staples of said at least one row against said anvil, said cartridge assembly comprising a driver mounted within said cartridge assembly and shiftable therein by said driver actuator between a retracted position and an extended position, a cartridge having at least one linear row of staple-containing first pockets at a first position aligned between said driver and said anvil, said driver having a plurality of blades equal in number to the number of said first pockets and configured to enter said first pockets and drive said staples therein through said tissue and against said anvil when shifted from said retracted position to said extended position by operation of said staple driver actuator, said cartridge assembly having at least one linear row of second pockets at a second position equal in number to said first pockets and each containing at least one staple, and indexing means to shift said plurality of first pockets out of said first position and said plurality of said second pockets into said first position after the first operation of said staple driver actuator to enable a second operation of said actuator.

47. The cartridge assembly claimed in claim 46, including a safety means to disable said indexing means until said first pockets are emptied by said driver.

48. A method of applying a plurality of surgical staples to tissue with a surgical stapling instrument of the type having a fixed jaw supporting an anvil, a movable jaw, a multiple load staple cartridge coupled to said movable jaw, a staple driver, and means for actuating said staple driver, comprising the steps of:

(a) positioning said tissue to be stapled between said anvil and said staple cartridge located on said movable jaw, said cartridge containing a first linear array of staples located in a first position within said cartridge aligned between said anvil and said driver, and a second array of staples located in a second position within said cartridge out of alignment with said anvil and said staple driver;

(b) adjusting said movable jaw toward said anvil so that said cartridge is spaced at a distance from said anvil such that said staples will be properly clinched against said anvil;

(c) operating said staple driver to drive said first array of staples from said first position in said cartridge through said tissue and against said anvil;

(d) adjusting said movable jaw away from said stapled tissue;
(e) releasing said stapled tissue from between said jaws of said instrument;
(f) operating an indexing means to transfer said second array of staples from said second position to said first position;
(g) repeating steps (a) through (e).

49. The method of claim 48, wherein the indexing step further includes the step of individually shifting each of said staples contained in said second array from said second position to said first position.

50. The method of claim 48, wherein the indexing step further includes the step of simultaneously shifting all of said staples contained in said second array from said second position to said first position.

* * * * *